United States Patent [19]
Schindler et al.

[11] Patent Number: 6,162,819
[45] Date of Patent: Dec. 19, 2000

[54] PYRAZOLE DERIVATIVES, THEIR PREPARATION AND THEIR USE IN PHARMACEUTICALS

[75] Inventors: Ursula Schindler, Bad Soden; Karl Schönafinger, Alzenau; Hartmut Strobel, Liederbach, all of Germany

[73] Assignee: Aventis Pharma Deutschland GmbH, Frankfurt am Main, Germany

[21] Appl. No.: 09/166,283

[22] Filed: Oct. 5, 1998

[30] Foreign Application Priority Data

Oct. 6, 1997 [DE] Germany .................... 197 44 026

[51] Int. Cl.$^7$ .................. A61K 31/4155; A61K 31/416; C07D 405/04

[52] U.S. Cl. .................. 514/405; 514/406; 548/368.1; 548/365.7

[58] Field of Search .................. 548/368.1, 365.7; 514/405, 406

[56] References Cited

U.S. PATENT DOCUMENTS

| | | | |
|---|---|---|---|
| 4,072,498 | 2/1978 | Moon et al. | 504/249 |
| 4,325,962 | 4/1982 | Rainer | 424/273 |
| 5,434,178 | 7/1995 | Talley et al. | 514/406 |
| 5,574,168 | 11/1996 | Kuo et al. | 548/360.5 |

FOREIGN PATENT DOCUMENTS

| | | |
|---|---|---|
| 0 667 345 A1 | 8/1995 | European Pat. Off. . |
| 2141124 | 2/1972 | Germany . |
| 2141125 | 2/1972 | Germany . |
| WO 98/16223 | 4/1998 | WIPO . |
| WO 98/16507 | 4/1998 | WIPO . |
| WO 98/23619 | 6/1998 | WIPO . |

OTHER PUBLICATIONS

Gnichtel et al., Chemical Abstracts, 111;57617, 1989.
Yoshina et al., Chemical Abstracts, 88:105211, 1978.
Shimanskaya et al., Chemical Abstracts, 69:112873, 1968.
Huang et al., Chemical Abstracts, 98:107203, 1993.
S. Guo, et al., "Preparation of condensed 1–benzyl–3–arylpyrazole derivatives as blood platelet aggregation inhibitors," *Chemical Abstracts*, Columbus, Ohio, US, (1996) vol. 125, No. 3, 125: 33633m, p. 903.
S. Yoshina et al., "Pyrazole derivatives," *Chemical Abstracts*, Columbus, Ohio, US, (1976) vol. 84, 84:180207p, p. 575.
S. M. Yu, et al., "Inhibition of Platelet Function by A02131–1, a Novel Inhibitor of cGMP–Specific Phosphodiesterase, In Vitro and In Vivo," *Blood*, (1996) vol. 87, No. 9, pp 3758–3767.
D. L. Vesely, "B complex vitamins activate rat guanylate cyclase and increase cyclic GMP levels," *European Journal of Clinical Investigation*, (1985) vol. 15, pp. 258–262.
D. L. Vesely, "Phencyclidine Stimulates Guanylate Cyclase Activity," *Biochemical and Biophysical Research Communications*, (1979) vol. 88, No. 4, pp. 1244–1248.

L. J. Ignarro, "Regulation of Cytosolic Guanylyl Cyclase by Porphyrins and Metalloporphyrins," *Advances in Pharmacology*, (1994) vol. 26, pp. 35–65.
D. J. Pettibone, et al., "A Structurally Novel Stimulator of Guanylate Cyclase With Long–Lasting Hypotensive Activity In The Dog," *European Journal of Pharmacology*, (1985) vol. 116, pp. 307–312.
S. M. Yu, et al., "Vasorelaxant effect of isoliquiritigenin, a novel soluble guanylate cyclase activator, in rat aorta," *British Journal of Pharmacology*, (1995) vol. 114, pp. 1587–1594.
F. N. Ko, et al., "YC–1, a Novel Activator of Platelet Guanylate Cyclase," *Blood*, (1994) vol. 84, No. 12, pp. 4226–4233.
S. M. Yu, et al., "Mechanism of anti–proliferation caused by YC–1, an indazole derviative, in cultured rat A10 vascular smooth–muscle cells," *Biochem. J.*, (1995) vol. 306, pp. 787–792.
C. C. Wu, et al., "YC–1 inhibited human platelet aggregation through NO–independent activation of soluble guanylate cyclase," *British Journal of Pharmacology*, (1995) vol. 116, pp. 1973–1978.

*Primary Examiner*—Fiona T. Powers
*Attorney, Agent, or Firm*—Finnegan, Henderson, Farabow, Garrett and Dunner, L.L.P.

[57] ABSTRACT

The present invention relates to pyrazole derivatives of the formula I, their preparation and their use in pharmaceuticals:

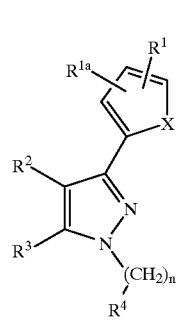

(I)

in which X, $R^1$, $R^{1a}$, $R^2$, $R^3$, $R^4$ and n are as defined in the claims, which are useful pharmaceutically active compounds for the therapy and prophylaxis of illnesses, for example of cardiovascular diseases such as hypertension, angina pectoris, cardiac insufficiency, thromboses or atherosclerosis. The compounds of the formula I are capable of modulating the body's production of cyclic guanosine monophosphate "cGMP" and are generally suitable for the therapy and prophylaxis of illnesses which are associated with a disturbed cGMP balance. The invention furthermore relates to processes for preparing compounds of the formula 1, to their use for the therapy and prophylaxis of the abovementioned illnesses and for preparing pharmaceuticals for this purpose, and also to pharmaceutical preparations which comprise the compounds of the formula I.

13 Claims, No Drawings

PYRAZOLE DERIVATIVES, THEIR PREPARATION AND THEIR USE IN PHARMACEUTICALS

This application claims the benefit of priority of German application 19744026.6, filed Oct. 6, 1997, and incorporates by reference that application.

The present invention relates to pyrazole derivatives of the formula I

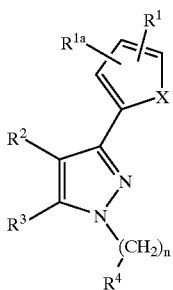

in which X, $R^1$, $R^{1a}$, $R^2$, $R^3$, $R^4$, and n are as defined below, which derivatives are useful pharmaceutically active compounds for the therapy and prophylaxis of illnesses, for example cardiovascular diseases such as hypertension, angina pectoris, cardiac insufficiency, thromboses, or atherosclerosis. The compounds of the formula I are capable of modulating the body's production of cyclic guanosine monophosphate "cGMP" and are generally suitable for the therapy and prophylaxis of illnesses which are associated with a disturbed cGMP balance. The invention furthermore relates to processes for preparing compounds of the formula 1, to their use for the therapy and prophylaxis of the abovementioned illnesses, to the methods of preparing pharmaceuticals for this purpose, and also to pharmaceutical preparations which comprise the compounds of the formula I.

cGMP is an important intracellular messenger which triggers a multitude of different effects via the modulation of cGMP-dependent protein kinases, phosphodiesterases and ion channels. Examples are the relaxation of smooth muscles, the inhibition of thrombocyte activation and the inhibition of the proliferation of smooth-muscle cells and of leukocyte adhesion. CGMP is produced by particulate and soluble guanylate cyclases "GC" as a response to a number of extra- and intracellular stimuli. In the case of the particulate guanylate cyclases, stimulation is essentially effected by peptidic messengers, such as the atrial natriuretic peptide or the cerebral natriuretic peptide. The soluble guanylate cyclases "sGC," which are cytosolic heterodimeric heme proteins, in contrast, are essentially regulated by a family of low-molecular-weight factors which are formed enzymatically. The most important stimulant is nitrogen monoxide "NO" or a closely related species. The function of other factors such as carbon monoxide or the hydroxyl radical is still largely unclear. Binding of NO to the heme with formation of a penta-coordinate heme-nitrosyl complex is being discussed as activation mechanism of the activation by NO. The associated release of the histidine which is bound in the basal state to the iron converts the enzyme into the active conformation.

Active soluble guanylate cyclases are in each case composed of an α and a β subunit. Several subunit subtypes have been described which differ from one another with respect to sequence, tissue-specific distribution and expression in different development stages. The subtypes $α_1$ and $β_1$ are mainly expressed in brain and lung, while $β_2$ is found in particular in liver and kidney. The subtype $α_2$ was shown to be present in human fetal brain. The subunits referred to as $α_3$ and $β_3$ were isolated from human brain and are homologous to $α_1$ and $β_1$. More recent works indicate an $α_{2i}$ subunit which contains an insert in the catalytic domain. All subunits show great homologies in the region of the catalytic domain. The enzymes presumably contain one heme per heterodimer, which is bound via $β_1$-Cys-78 and/or $β_1$-His-105 and is part of the regulatory center.

Under pathologic conditions, the formation of guanylate-cyclase-activating factors can be reduced, or their degradation may be promoted owing to the increased occurrence of free radicals. The resulting reduced activation of the sGC leads, via a weakening of the respective cGMP-mediated cellular response, for example to an increase of the blood pressure, to platelet activation or to increased cell proliferation and cell adhesion. As a consequence, formation of endothelial dysfunction, atherosclerosis, hypertension, stable and unstable angina pectoris, thromboses, myocardial infarction, strokes or erectile dysfunction results. Pharmacological stimulation of sGC offers a possibility to normalize cGMP production and therefore makes possible the treatment and/or prevention of such disorders.

For the pharmacological stimulation of the sGC, use has hitherto almost exclusively been made of compounds whose activity is based on an intermediate NO release, for example organic nitrates. The drawback of this treatment is the development of tolerance and a reduction of activity, and the higher dosage which is required because of this.

Various sGC stimulators which do not act via NO release were described by Veseley in a quite large number of applications. However, the compounds, most of which are hormones, plant hormones, vitamins or, for example, natural compounds such as lizard poisons predominantly only have weak effects on the cGMP formation in cell lysates (D. L. Veseley, *Eur. J. Clin. Invest.* 15 (1985) 258; D. L. Veseley, *Biochem. Biophys. Res. Comm.* 88 (1979) 1244). A stimulation of heme-free guanylate cyclase by protoporphyrin IX was demonstrated by lgnarro et al. (*Adv. Pharmacol.* 26 (1994) 35). Pettibone et al. (*Eur. J. Pharmacol.* 116 (1985) 307) described an antihypertensive action of diphenyliodonium hexafluorophosphate and attributed this to a stimulation of sGC. According to Yu et al. (*Brit. J. Pharmacol.* 114 (1995) 1587), isoliquiritigenin, which has a relaxing action on isolated rat aortas, also activates sGC. Ko et al. (*Blood* 84 (1994) 4226), Yu et al. (*Biochem. J.* 306 (1995) 787) and Teng et al. (*Brit. J. Pharmacol.* 116 (1995) 1973) demonstrated a sGC-stimulating activity of 1-benzyl-3-(5-hydroxymethyl-2-furyl)indazole and demonstrated an antiproliferative and thrombocyte-inhibiting action. EP-A-667 345 describes various indazoles as inhibitors of thrombocyte aggregation.

Surprisingly, it has not been reported until now that the pyrazole derivatives of the formula I effect guanylate cyclase activation and are therefore suitable for the therapy and prophylaxis of disorders which are associated with a low cGMP level.

Thus, the present invention relates to compounds of the formula I

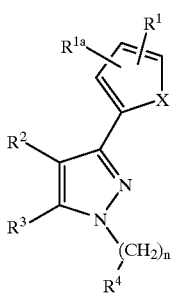

(I)

in which

X is O, S, NH or N(CH$_3$);

R$^1$ and R$^{1a}$ are identical or different, and are hydrogen, halogen, OR$^6$, NR$^7$R$^8$, CO—OR$^9$, CO—R$^{10}$, CO—NR$^{11}$R$^{12}$, CO—NR$^{12}$—OR$^{11}$, S(O)$_m$-R$^{13}$ S(O)$_2$-NR$^{14}$R$^{15}$, CN, NO$_2$, (C$_1$–C$_{10}$)-alkyl, (C$_6$–C$_{14}$)-aryl, (C$_6$–C$_{14}$)-aryl-(C$_1$–C$_4$)-alkyl, (C$_3$–C$_7$)-cycloalkyl, (C$_3$–C$_7$)-cycloalkyl-(C$_1$–C$_4$)-alkyl, the radical Het or the radical Het-(C$_1$–C$_4$)-alkyl, where alkyl radicals, aryl radicals, arylalkyl radicals, cycloalkyl radicals, cycloalkylalkyl radicals, radicals Het and radicals Het-alkyl representing R$^1$ or R$^{1a}$ may in each case be unsubstituted or substituted by one or more substituents R$^5$, and where R$^1$ can be NO$_2$ only in the case when simultaneously R$^{1a}$ is hydrogen, the radicals R$^2$ and R$^3$ together with the carbon atoms which carry them form an unsubstituted benzene ring or a benzene ring which is substituted by one or more substituents R$^5$, and the radical —(CH$_2$)$_n$-R$^4$ is different from unsubstituted phenyl;

R$^2$ and R$^3$ are identical or different, and are hydrogen, (C$_1$–C$_{10}$)-alkyl, (C$_6$–C$_{14}$)-aryl, (C$_6$–C$_{14}$)-aryl-(C$_1$–C$_4$)-alkyl, (C$_3$–C$_7$)-cycloalkyl, (C$_3$–C$_7$)-cycloalkyl-(C$_1$–C$_4$)-alkyl, the radical Het or the radical Het-(C$_1$–C$_4$)-alkyl, where alkyl radicals, aryl radicals, arylalkyl radicals, cycloalkyl radicals, cycloalkylalkyl radicals, radicals Het and radicals Het-alkyl representing R$^2$ or R$^3$ may in each case be unsubstituted or substituted by one or more substituents R$^5$, or R$^2$ and R$^3$ together with the carbon atoms which carry them form a 5- to 7-membered carbocyclic ring which may contain one or more double bonds and which may be unsubstituted or substituted by one or more substituents R$^5$;

R$^4$ is hydrogen, (C$_1$–C$_{10}$)-alkyl, (C$_6$–C$_{14}$)-aryl, (C$_6$–C$_{14}$)-aryl-(C$_1$–C$_4$)-alkyl, (C$_3$–C$_7$)-cycloalkyl, (C$_3$–C$_7$)-cycloalkyl-(C$_1$–C$_4$)-alkyl, the radical Het or the radical Het-(C$_1$–C$_4$)-alkyl, where alkyl radicals, aryl radicals, arylalkyl radicals, cycloalkyl radicals, cycloalkylalkyl radicals, radicals Het and radicals Het-alkyl representing R$^4$ may in each case be unsubstituted or substituted by one or more substituents R$^5$, and where, if n=0, R$^4$ may not be hydrogen;

n is 0, 1 or 2;

Het is a 5- to 7-membered, saturated or unsaturated heterocycle;

R$^5$ is halogen, (C$_1$–C$_5$)-alkyl, OR$^6$, NR$^6$R$^8$, CO—OR$^9$, CO—R$^{10}$, CO—NR$^{11}$R$^{12}$ CO—NR$^{12}$—OR$^{11}$, S(O)$_m$—R$^{13}$, S(O)$_2$—NR$^{14}$R$^{15}$, NO$_2$, CN or CF$_3$, where radicals R$^5$ that occur more than once are identical or different;

R$^6$, R$^7$, R$^8$, R$^{11}$ and R$^{14}$ are identical or different, and are hydrogen, (C$_1$–C$_{10}$)-alkyl, (C$_6$–C$_{14}$)-aryl, (C$_6$–C$_{14}$)-aryl-(C$_1$–C$_4$)-alkyl, (C$_3$–C$_7$)-cycloalkyl, (C$_3$–C$_7$)-cycloalkyl-(C$_1$–C$_4$)-alkyl, the radical Het, the radical Het-(C$_1$–C$_4$)-alkyl, CO—R$^{16}$ or S(O)$_2$-R$^{17}$, where alkyl radicals, aryl radicals, arylalkyl radicals, cycloalkyl radicals, cycloalkylalkyl radicals, radicals Het and radicals Het-alkyl representing R$^6$, R$^7$, R$^8$, R$^{11}$ and R$^{14}$ may in each case be unsubstituted or substituted by one or more identical or different substituents selected from the group consisting of halogen, (C$_1$–C$_5$)-alkyl, OR$^{18}$, NR$^{19}$R$^{20}$, CO—OR$^{21}$, CO—R$^{22}$, CO—NR$^{23}$R$^{24}$, CO—NR$^{24}$—OR$^{23}$ S(O)$_m$—R$^{25}$, S(O)$_2$—NR$^{26}$R$^{27}$, NO$_2$, CN and CF$_3$, and where radicals R$^6$, R$^7$, R$^8$, R$^{11}$ and R$^{14}$ that occur more than once are identical or different;

R$^9$, R$^{10}$, R$^{12}$, R$^{13}$ and R$^{15}$ are identical or different, and are hydrogen, (C$_1$–C$_{10}$)-alkyl, (C$_6$–C$_{14}$)-aryl, (C$_6$–C$_{14}$)-aryl-(C$_1$–C$_4$)-alkyl, (C$_3$–C$_7$)-cycloalkyl, (C$_3$–C$_7$)-cycloalkyl-(C$_1$–C$_4$)-alkyl, the radical Het or the radical Het-(C$_1$–C$_4$)-alkyl, where alkyl radicals, aryl radicals, arylalkyl radicals, cycloalkyl radicals, cycloalkylalkyl radicals, radicals Het and radicals Het-alkyl representing R$^9$, R$^{10}$, R$^{12}$, R$^{13}$ and R$^{15}$ may in each case be unsubstituted or substituted by one or more identical or different substituents selected from the group consisting of halogen, (C$_1$–C$_5$)-alkyl, OR$^{18}$, NR$^{19}$R$^{20}$, CO—OR$^{21}$, CO—R$^{22}$, CO—NR$^{23}$R$^{24}$, CO—NR$^{24}$—OR$^{23}$, S(O)$_m$—R$^{25}$, S(O)$_2$—NR$^{26}$R$^{27}$, NO$_2$, CN and CF$_3$, and where radicals R$^9$, R$^{10}$, R$^{12}$, R$^{13}$ and R$^{15}$ that occur more than once are identical or different; or the two radicals R$^7$ and R$^8$, the two radicals R$^{11}$ and R$^{12}$ and the two radicals R$^{14}$ and R$^{15}$, in each case together with the nitrogen atom which carries the two radicals, form a 5- to 7-membered, saturated or unsaturated heterocyclic ring which may contain an additional ring heteroatom selected from the group consisting of nitrogen, oxygen and sulfur and which may be substituted by one or more identical or different substituents selected from the group consisting of (C$_1$–C$_4$)-alkyl and halogen;

R$^{16}$ is hydrogen, (C$_1$–C$_6$)-alkyl, (C$_3$–C$_7$)-cycloalkyl, (C$_3$–C$_7$)-cycloalkyl-(C$_1$–C$_4$)-alkyl, (C$_6$–C$_{14}$)-aryl, (C$_6$–C$_{14}$)-aryl-(C$_1$–C$_4$)-alkyl, the radical Het or the radical Het-(C$_1$–C$_4$)-alkyl;

R$^{17}$ is (C$_1$–C$_6$)-alkyl, (C$_3$–C$_7$)-cycloalkyl, (C$_3$–C$_7$)-cycloalkyl-(C$_1$–C$_4$)-alkyl, (C$_6$–C$_{14}$)-aryl, (C$_6$–C$_{14}$)-aryl-(C$_1$–C$_4$)-alkyl, the radical Het or the radical Het-(C$_1$–C$_4$)-alkyl;

R$^{18}$, R$^{19}$, R$^{20}$, R$^{23}$ and R$^{26}$ are identical or different, and are hydrogen, (C$_1$–C$_{10}$)-alkyl, (C$_3$–C$_7$)-cycloalkyl, (C$_3$–C$_7$)-cycloalkyl-(C$_1$–C$_4$)-alkyl, (C$_6$–C$_{14}$)-aryl, (C$_6$–C$_{14}$)-aryl-(C$_1$–C$_4$)-alkyl, the radical Het, the radical Het-(C$_1$–C$_4$)-alkyl, CO—R$^{16}$ or S(O)$_2$—R$^{17}$, where radicals R$^{18}$, R$^{19}$, R$^{20}$, R$^{23}$ and R$^{26}$ that occur more than once are identical or different;

R$^{21}$, R$^{22}$, R$^{24}$, R$^{25}$ and R$^{27}$ are identical or different, and are hydrogen, (C$_1$–C$_{10}$)-alkyl, (C$_3$–C$_7$)-cycloalkyl, (C$_3$–C$_7$)-cycloalkyl-(C$_1$–C$_4$)-alkyl, (C$_6$–C$_{14}$)-aryl, (C$_6$–C$_{14}$)-aryl-(C$_1$–C$_4$)-alkyl, the radical Het or the radical Het-(C$_1$–C$_4$)-alkyl, where radicals R$^{21}$, R$^{22}$, R$^{24}$, R$^{25}$ and R$^{27}$ that occur more than once are identical or different, or the two radicals R$^{19}$ and R$^{20}$, the two radicals R$^{23}$ and R$^{24}$ and the two radicals R$^{25}$ and R$^{27}$, in each case together with the nitrogen atom which carries the two radicals, form a 5- to 7-membered, saturated or unsaturated heterocyclic ring which may contain an additional ring heteroatom selected from the group consisting of nitrogen, oxygen and sulfur and which may be substituted by one or more identical or different substituents selected from the group consisting of $(C_1-C_4)$-alkyl and halogen;

m is 0, 1 or 2;

in all their stereoisomer forms and mixtures thereof in all ratios, and their physiologically acceptable salts;

except for compounds of the formula I where the following radicals simultaneously have the following meanings: $R^1$ is a radical in the 5-position of the furan ring, thiophene ring or pyrrole ring selected from the group consisting of hydrogen, $(C_1-C_3)$-alkyl, COOH, CO—O—$(C_1-C_3)$-alkyl, $CH_2$—OH, $CH_2$—O—$(C_1-C_3)$-alkyl and halogen; $R^{1a}$ is hydrogen; $R^2$ and $R^3$ together with the carbon atoms which carry them are a benzene ring which is unsubstituted or monosubstituted by a radical selected from the group consisting of $(C_1-C_3)$-alkyl, halogen, hydroxyl and $(C_1-C_3)$-alkoxy; n is the number 1; $R^4$ is unsubstituted phenyl or phenyl which is monosubstituted by a radical selected from the group consisting of $(C_1-C_3)$-alkyl, halogen, hydroxyl and $(C_1-C_3)$-alkoxy; and except for the compound of the formula I where the radicals simultaneously have the following meanings: X is S; $R^1$ is a chlorine atom which is attached to the 5-position of the thiophene ring; $R^{1a}$ is hydrogen; $R^2$ is methyl; $R^3$ is hydrogen; n is 0; $R^4$ is the radical $(CH_3)_2N$—CO—$CH(CH_3)$—.

Alkyl radicals may be straight-chain or branched. This also applies when they are substituted, for example by an aryl radical in an arylalkyl group or by the radical Het in the group Het-alkyl or when they are part of other groups, for example in alkoxy groups, alkoxycarbonyl groups or N-alkyl-substituted carbamoyl groups. Examples of alkyl groups are methyl, ethyl, n-propyl, isopropyl, n-butyl, isobutyl, sec-butyl, tert-butyl, n-pentyl, isopentyl, neopentyl, n-hexyl, 3,3-dimethylbutyl, n-heptyl, n-octyl, n-nonyl and n-decyl. The term alkyl here also includes unsaturated alkyl radicals, in particular alkyl radicals which contain one or two double bonds or one or two triple bonds or a double bond and a triple bond. Examples of such radicals are the vinyl radical, the 2-propenyl radical (allyl radical), the 2-butenyl radical, the 3-methyl-2-butenyl radical, the ethinyl radical, the 2-propinyl radical (propargyl radical) or the 3-butinyl radical.

Examples of cycloalkyl radicals are cyclopropyl, cyclobutyl, cyclopentyl, cyclohexyl and cycloheptyl. Cycloalkyl radicals may also be substituted by alkyl groups, for example by one or more methyl groups.

Examples of $(C_6-C_{14})$-aryl radicals are phenyl, naphthyl, anthracenyl, biphenylyl or fluorenyl, where the polynuclear radicals may be linked via all positions. Thus, naphthyl radicals, for example, may be present as 1-naphthyl radicals or 2-naphthyl radicals. A preferred aryl radical is the phenyl radical. Aryl radicals may be unsubstituted or mono- or polysubstituted, for example di- or trisubstituted, and the substituents may be in any position. Monosubstituted phenyl radicals may be substituted in the 2-position, the 3-position or the 4-position, disubstituted phenyl radicals in the 2,3-position, the 2,4-position, the 2,5-position, the 2,6-position, the 3,4-position or the 3,5-position. In trisubstituted phenyl radicals, the substituents may be, for example, in 2,3,4-position, 2,3,5-position, 2,3,6-position or 3,4,5-position. These illustrations for aryl radicals also apply to those aryl radicals which are part of arylalkyl radicals, for example of benzyl radicals, 1-phenylethyl radicals, 2-phenylethyl radicals or naphthylmethyl radicals. Preferred arylalkyl radicals are phenylethyl radicals and in particular the benzyl radical.

The 5- to 7-membered, saturated or unsaturated, heterocycles representing the group Het preferably contain one, two, three or four ring heteroatoms selected from the group consisting of nitrogen, oxygen and sulfur. Particularly preferably, they contain one, two or three heteroatoms from this group. Unsaturated heterocycles may contain one, two or three double bonds in the ring. The 5-membered ring and 6-membered ring heterocycles may in particular also be aromatic, i.e., Het in the compounds of the formula I may also be 5- or 6-membered hetaryl which may be unsubstituted or substituted. Examples of heterocyclic 5-membered ring, 6-membered ring and 7-membered ring systems from which the radicals in question may be derived are pyrrole, furan, thiophene, imidazole, pyrazole, 1,2,3-triazole, 1,2,4-triazole, 1,3-dioxole, 1,3-oxazole, 1,2-oxazole, 1,3-thiazole, 1,2-thiazole, tetrazole, pyridine, pyridazine, pyrimidine, pyrazine, pyran, thiopyran, 1,4-dioxine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, 1,2,4,5-tetrazine, azepine, 1,2-diazepine, 1,3-diazepine, 1,4-diazepine, 1,3-oxepine or 1,3-thiazepine, all in each case in saturated form (perhydro form) or in partially unsaturated form (dihydro form and tetrahydro form) or in maximally unsaturated form (aromatic form in the case of the 5-membered rings and 6-membered rings), insofar as the forms in question are known and stable. Thus, the heterocycles which are suitable also include, for example, the saturated heterocycles pyrrolidine, piperidine, piperazine, morpholine and thiomorpholine.

The heterocyclic radical may be attached via any carbon atom, i.e., for example, in the case of radicals which are derived from the furan system, the thiophene system or the pyrrole system, it may be attached in the 2-position or the 3-position, in the case of radicals derived from the imidazole system or from the 1,3-thiazole system, it may be attached in the 2-position, the 4-position or the 5-position, or in the case of radicals which are derived from the pyridine system, it may be attached in the 2-position, the 3- position or the 4-position. Nitrogen heterocycles, which may carry a substituent at a ring nitrogen atom, may also be attached via a ring nitrogen atom if the heterocyclic radical in question is attached to a carbon atom. The heterocycles may be mono- or polysubstituted, for example disubstituted, trisubstituted or tetrasubstituted, and may be substituted in any positions. Substituents on a heterocycle may also form a ring, i.e. condensed heterocycles may be present, for example cyclopenta-condensed, cyclohexa-condensed or benzo-condensed heterocycles. Suitable substituents at a nitrogen atom of a heterocycle are in particular, for example, $(C_1-C_5)$-alkyl radicals or the radicals CO—$R^{16}$ or $SO_2$—$R^{17}$, but also, for example, aryl radicals or arylalkyl radicals. Nitrogen heterocycles may also be present as N-oxides.

Halogen is, unless stated otherwise, fluorine, chlorine, bromine or iodine, preferably fluorine or chlorine.

If alkyl radicals, aryl radicals, arylalkyl radicals, cycloalkyl radicals, cycloalkylalkyl radicals or the radicals Het or Het-alkyl are substituted by radicals $R^5$, they may be substituted by one, two, three, four or more identical or different radicals $R^5$. Such substituted radicals preferably contain one, two or three identical or different radicals $R^5$. In the case of the arylalkyl radicals, cycloalkylalkyl radicals and the radicals Het-alkyl, the radicals $R^5$ may in each case be in the alkyl moiety and/or in the aryl moiety and/or cycloalkyl moiety and/or the radical Het. If $R^2$ and $R^3$ together with the carbon atoms which carry them form a carbocyclic ring which is substituted by one or more radicals R⁵, this ring is preferably substituted by one, two, three or four identical or different radicals R⁵, particularly preferably by one or two radicals. The radicals R⁵ may be in any positions.

The two substituents $R^1$ and $R^{1a}$ may be in any positions of the heterocycle, i.e. in the positions 3, 4 and 5 of the furan ring, thiophene ring or pyrrole ring.

If $R^2$ and $R^3$ together with the carbon atoms which carry them form a 5- to 7-membered carbocyclic ring, condensed pyrazoles are present. In the case of a fused-on 5-membered ring, i.e. in the case of cyclopenta-condensed pyrazoles, the carbocyclic ring may, in addition to the double bond that it shares with the pyrazole ring, contain a further double bond in the ring or no further double bonds in the ring. In the case of a fused-on 6-membered ring (i.e. in the case of cyclohexa-condensed pyrazoles) or in the case of a fused-on 7-membered ring (i.e. in the case of a cyclohepta-condensed pyrazole) the carbocyclic ring may, in addition to the double bond which it shares with the pyrazole ring, contain a further double bond in the ring or two further double bonds in the ring or no further double bonds in the ring. The double bonds in the carbocyclic ring may be in any positions, but cumulated double bond systems may not be present. If $R^2$ and $R^3$ together with the carbon atoms which carry them form a 6-membered carbocycle having a total of three double bonds, a benzene ring is fused to the pyrazole ring, the compounds of the formula I are in this case benzo-pyrazoles (formula Ia) which are also called indazoles (the compounds according to the invention are 1Hindazoles just as the non-benzo-fused pyrazoles are 1H-pyrazoles). Examples of such compounds of the formula I in which $R^2$ and $R^3$ together with the carbon atoms which carry them form a carbocyclic ring are the compounds of the formulae Ia, Ib, Ic and Id, in which X, $R^1$, $R^{1a}$, $R^4$, $R^5$ and n are as defined above and y, in accordance with the statements above, is 0 or an integer, preferably 0, 1, 2, 3 or 4, particularly preferably 0, 1 or 2. The radicals $R^5$, which may be identical or different, may be in any positions in the carbocycle.

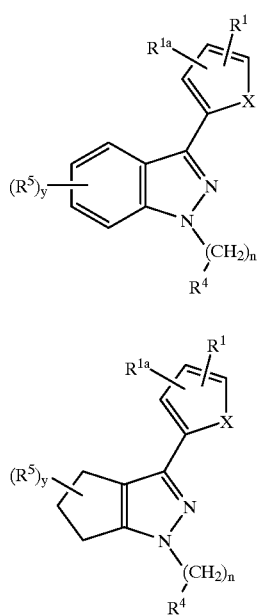

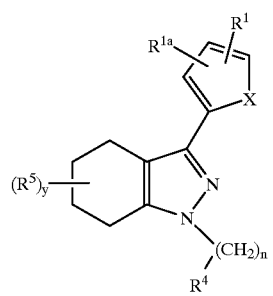

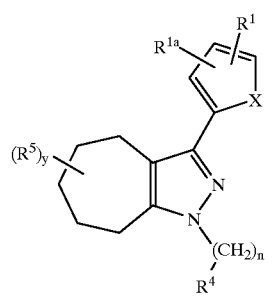

The heterocyclic rings which may be formed by the two radicals $R^7$ and $R^8$, the two radicals $R^{11}$ and $R^{12}$, the two radicals $R^{14}$ and $R^{15}$, the two radicals $R^{19}$ and $R^{20}$, the two radicals $R^{23}$ and $R^{24}$ and the two radicals $R^{26}$ and $R^{27}$, in each case together with the nitrogen atom which carries the two radicals, may be saturated or partially unsaturated or maximally unsaturated. They are preferably saturated. Examples of such rings which are attached via a ring nitrogen atom to a carbonyl group or a sulfonyl group are in particular pyrroline, pyrrolidine, piperidine, piperazine, morpholine and thiomorpholine. These rings may be substituted at carbon atoms and, in the case of piperazine, also at the nitrogen atom in the 4-position, and may also be, in the case of the thiomorpholine, be oxidized at the sulfur to the sulfoxide or to the sulfone.

If n in the formula I is the number 0, the radical $R^4$ is attached directly to the pyrazole nitrogen atom.

If they are appropriately substituted, the compounds of the formula I may be present in stereoisomeric forms. If the compounds of the formula I contain one or more centers of symmetry, these are identical or different from each other and have the S configuration or the R configuration. The invention includes all possible stereoisomers, for example enantiomers and diastereomers, and mixtures of two or more stereoisomeric forms, for example mixtures of enantiomers and/or diastereomers, in all ratios. Thus, the invention provides enantiomers in enantiomerically pure form, both as levorotatory and as dextrorotatory antipodes, in the form of racemates and in the form of mixtures of the two enantiomers in all ratios. In the case of a cisitrans isomerism, the invention provides both the cis form and the trans form and mixtures of these forms. The preparation of individual stereoisomers can be carried out, if desired, by separation of a mixture by customary methods, for example by chromatography or crystallization, by the use of stereochemically uniform starting materials for the synthesis or by stereoselective synthesis. The separation of a mixture of stereoisomers can be carried out at the stage of the compounds of the formula I or during the synthesis.

If mobile hydrogen atoms are present, the present invention also includes all tautomeric forms of the compounds of the formula I, for example lactam/lactim tautomers.

If the compounds of the formula I contain one or more acidic or basic groups, the invention also provides the corresponding physiologically or toxicologically tolerable salts, in particular the pharmaceutically acceptable salts. Thus, the compounds of the formula I which contain one or more acidic groups, for example COOH groups or N-acylsulfonamido groups, may be present on these groups and may be used according to the invention, for example as alkali metal salts, alkaline earth metal salts or as ammonium salts. Examples of such salts are sodium salts, potassium salts, calcium salts, magnesium salts or salts with ammonia or organic amines, such as, for example, ethylamine, ethanolamine, triethanolamine or amino acids. Compounds of the formula I which contain one or more basic groups, i.e., groups which can be protonated, can be present and can be used according to the invention in the form of their acid addition salts with inorganic or organic acids which, for example as salts with hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc.

If the compounds of the formula I simultaneously contain acidic and basic groups in the molecule, the invention also includes, in addition to the salt forms mentioned, inner salts, so-called betaines. Salts can be obtained from the compounds of the formula I by customary methods which are known to the person skilled in the art, for example by combination with an organic or inorganic acid or base in a solvent or dispersant, or else by anion exchange or cation exchange from other salts. The present invention also includes all salts of the compounds of the formula I which, owing to low physiological compatibility, are not directly suitable for use in pharmaceuticals but which can be used, for example, as intermediates for chemical reactions or for the preparation of physiologically acceptable salts.

The present invention furthermore includes all solvates of compounds of the formula I, for example hydrates or adducts with alcohols, and also derivatives of the compounds of the formula I,for example esters, prodrugs and metabolites, which act like the compounds of the formula I.

In the formula I, X is preferably O or S, and most preferably O.

$R^1$ is preferably $(C_1-C_{10})$-alkyl which is substituted by hydroxyl, in particular $CH_2OH$ or $CH(OH)$—$((C_1-C_5)$-alkyl), or is CO—$OR^9$ or CO—$NR^{11}R^{12}$. Particularly preferably, the radical $R^1$ is in the 5-position of the heterocycle. $R^{1a}$ is preferably hydrogen.

$R^2$ and $R^3$ preferably form, together with the carbon atoms which carry them, a benzene ring which may be unsubstituted or substituted by one or more identical or different substituents $R^5$ (the compounds according to the invention in which $R^2$ and $R^3$ have these preferred meanings are the benzo-condensed pyrazoles of the formula Ia).

n is preferably 0 or 1.

$R^4$ is preferably $(C_6-C_{14})$-aryl, in particular phenyl, or 5- or 6-membered heteroaryl, it being possible for these radicals to be substituted or unsubstituted.

Radicals $R^5$ which are present in the radicals $R^2$ and $R^3$ are preferably halogen, $(C_1-C_3)$-alkyl, $CF_3$, $(C_1-C_3)$-alkyl-O or $S(O)_2$—$NR^{14}R^{15}$, particularly preferably $CF_3$, radicals $R^5$ which are present in the radical $R^4$ are preferably halogen, $(C_1-C_3)$-alkyl, or $CF_3$.

$R^6$ is preferably hydrogen or $(C_1-C_3)$-alkyl.

$R^7$ is preferably hydrogen, $(C_1-C_3)$-alkyl, CO—$R^{16}$ or $S(O)_2$—$R^{17}$.

$R^8$ is preferably hydrogen.

$R^9$ is preferably $CH_2CH_2$—OH or $CH_2CH_2$—$NR^{19}R^{20}$.

$R^{10}$ is preferably $(C_1-C_3)$-alkyl or unsubstituted or substituted phenyl.

$R^{11}$ is preferably hydrogen.

$R^{12}$ is preferably unsubstituted $(C_1-C_4)$-alkyl, $(C_1-C_4)$-alkyl which is substituted by a radical selected from the group consisting of $OR^{18}$, $NR^{19}$, $R^{20}$ and CO—$NR^{23}$, $R^{24}$, 5- or 6-membered heteroaryl, unsubstituted phenyl or phenyl which is substituted by one, two or three identical or different radicals selected from the group consisting of halogen, $(C_1-C_5)$-alkyl, $OR^{18}$, $NR^{19}R^{20}$, CO—$OR^{21}$, CO—$R^{22}$, CO—$NR^{23}R^{24}$, $S(O)mR^{25}$, $S(O)_2$—$NR^{26}R^{27}$, $NO_2$, CN and $CF_3$.

$R^{13}$ is preferably $(C_1-C_3)$-alkyl, unsubstituted phenyl, phenyl which is substituted by one, two or three identical or different radicals selected from the group consisting of halogen, $(C_1-C_5)$-alkyl, $OR^{18}$, $NR^{19}R^{20}$, CO—$OR^{21}$, CO—$R^{22}$, CO—$NR^{23}R^{24}$, $S(O)_m$—$R^{25}$, $S(O)_2$—$NR^{26}R^{27}$, $NO_2$, CN and $CF_3$, or is 5- or 6-membered heteroaryl.

$R^{14}$ is preferably $(C_1-C_3)$-alkyl, 5- or 6-membered heteroaryl, CO—$R^{16}$, unsubstituted phenyl or phenyl which is substituted by one, two or three identical or different radicals selected from the group consisting of halogen, $(C_1-C_5)$-alkyl, $OR^{18}$, $NR^{19}R^{20}$, CO—$OR^{21}$, CO—$R^{22}$, CO—$NR^{23}R^{24}$, $S(O)_m$—$R^{25}$, $S(O)_2$—$NR^{26}R^{27}$, $NO_2$, CN and $CF_3$.

$R^{15}$ is preferably hydrogen.

It is also preferred when the radicals $R^{14}$ and $R^{15}$ together with the nitrogen atom which carries the two radicals form a 5- to 7-membered saturated ring which, particularly preferably, contains an oxygen atom, a sulfur atom or a nitrogen atom which is substituted by a methyl group as additional ring heteroatom.

$R^{16}$ is preferably $(C_1-C_3)$-alkyl.

$R^{17}$ is preferably $(C_1-C_3)$-alkyl.

$R^{18}$ is preferably hydrogen or $(C_1-C_3)$-alkyl.

$R^{19}$ is preferably hydrogen.

$R^{20}$ is preferably CO—$(C_1-C_3)$-alkyl or CO—$(C_6-C_{14})$-aryl, $S(O)_2$-$(C_1-C_3)$-alkyl or $S(O)_2$-$(C_6-C_{14})$-aryl.

$R^{21}$, $R^{22}$, $R^{24}$ and $R^{25}$ are preferably $(C_1-C_3)$-alkyl.

$R^{23}$ is preferably hydrogen or $(C_1-C_3)$-alkyl.

$R^{26}$ is preferably $(C_1-C_3)$-alkyl or CO—$R^{16}$.

$R^{27}$ is preferably hydrogen.

It is also preferred when $R^{26}$ and $R^{27}$ together with the nitrogen atom which carries the two radicals form a 5- to 7-membered saturated ring which, particularly preferably, contains an oxygen atom, a sulfur atom or a nitrogen atom which is substituted by a methyl group as additional ring heteroatom.

A 5- or 6-membered heteroaryl radical is preferably the radical of an aromatic heterocycle having one, two, three or four heteroatoms selected from the group consisting of nitrogen, oxygen and sulfur, particularly preferably having one or two heteroatoms or the tetrazolyl radical. Very particularly preferably, a 5- or 6-membered heteroaryl radical is the radical of one of the aromatic heterocycles furan, thiophene, 1,3-thiazole, 1,3-oxazole, 1,2-oxazole, tetrazole, pyridine and pyrimidine, and additionally, preferably, of 1,3-thiazole or of tetrazole. These radicals are attached via a carbon atom and can be unsubstituted or substituted as mentioned above.

Preferred compounds of the formula I are those in which one or more of the radicals contained therein have preferred meanings, all combinations of preferred substituent definitions being included. The present invention also includes all stereoisomeric forms and mixtures thereof in all ratios, and the physiologically acceptable salts, of all preferred compounds of the formula I.

The compounds of the formula I can be prepared by various processes, which are described hereinbelow and which also form part of the subject matter of the present invention. Compounds of the formula I in which the radicals $R^2$ and $R^3$ together with the carbon atoms which carry them do not form a benzene ring, i.e., in which the radicals $R^2$ and $R^3$ are hydrogen or an unsubstituted or substituted alkyl radical, aryl radical, arylalkyl radical, cycloalkyl radical, cycloalkylalkyl radical, the radical Het or the radical Hetalkyl or in which $R^2$ and $R^3$ together with the carbon atoms which carry them form an unsubstituted or substituted nonaromatic carbocyclic ring can be prepared by reacting 1,3-dicarbonyl compounds of the formula II with hydrazines of the formula III or salts thereof to give compounds of the formula Ie'. In the formulae II and III and in the formula Ie', the radicals X, $R^{1'}$, $R^{1a'}$, $R^{2'}$, $R^{3'}$ and $R^{4'}$ and the number n may have the abovementioned meanings of X, $R^1$, $R^{1a}$, $R^2$, $R^3$, $R^4$ and n, but the radicals $R^{2'}$ and $R^{3'}$ together with the carbon atoms which carry them may not form an aromatic ring, and additionally functional groups in the radicals $R^{1'}$, $R^{1a'}$, $R^{2'}$, $R^{3'}$ and $R^{4'}$ may be present in protected form or in the form of precursors.

Suitable protective groups or favorable precursors for functional groups in these radicals are known to the person skilled in the art. For example, a carbonyl group in these radicals may initially be present in protected form, for example in the form of an acetal or ketal, or an amino group may be present in acylated form, or a hydrogen atom may be present as a precursor for a group which is introduced in an electrophilic substitution reaction. If appropriate, compounds of the formula Ie according to the invention can then be obtained from compounds of the formula Ie' by converting thegroups which are present in protected form or in the form of precursors in a subsequent reaction step into the desired functional groups mentioned in the above definitions of $R^1$, $R^{1a}$, $R^2$, $R^3$ and $R^4$.

cycloalkylalkyl radical, the radical Het or the radical Hetalkyl, or $R^2$ and $R^3$ together with the carbon atoms which carry them form an unsubstituted or substituted nonaromatic 5- to 7-membered carbocyclic ring.

Reactions of compounds of the formula II with the hydrazines of the formula III or salts thereof are preferably carried out in a solvent or dispersant. Suitable solvents are for example, water, alcohols, such as methanol, ethanol, n-propanol, isopropanol or butanols, ethers, such as diethyl ether, dipropyl ether, dibutyl ether, methyl-tert-butyl ether, tetrahydrofuran or dioxane, monoethers and diethers of ethylene glycol and of di- and triethylene glycol, such as ethylene glycol monomethyl ether, ethylene glycol monoethyl ether, ethylene glycol dimethyl ether, ethylene glycol monobutyl ether, diethylene glycol monomethyl ether or diethylene glycol dimethyl ether, esters, such as ethyl acetate or butyl acetate, amides, such as dimethylformamide, dimethylacetamide, N-methylpyrrolidone or hexamethylphosphoric triamide, nitriles, such as acetonitrile, acids such as acetic acid, sulfoxides and sulfones, such as dimethyl sulfoxide or sulfolane, hydrocarbons and chlorinated hydrocarbons, such as petroleum fractions, benzene, toluene, xylene, chlorobenzene, dichlorobenzene, methylene chloride or chloroform. It is also possible to employ mixtures of two or more solvents, for example mixtures of water and alcohols, mixtures of water and acids or mixtures of alcohols and acids. Preferred solvents are alcohols such as methanol and ethanol.

The reaction is generally carried out at temperatures from 0° C. to 150° C., preferably at temperatures from 20° C. to 1 30° C.. Particular preference is given to carrying out the reaction under reflux at the boiling point of the solvent or solvent mixture used, for example at the boiling point of methanol or ethanol. The reaction time is determined by the individual case and depends, for example, on the reactivity of the reactants and the reaction conditions. The reaction is generally complete after 1 to 10 hours if the reaction is carried out in methanol or ethanol at boiling point. The work-up of the reaction mixture can be carried out by standard methods, and the product can, if desired, be purified by customary purification methods, for example by recrystallization or chromatography.

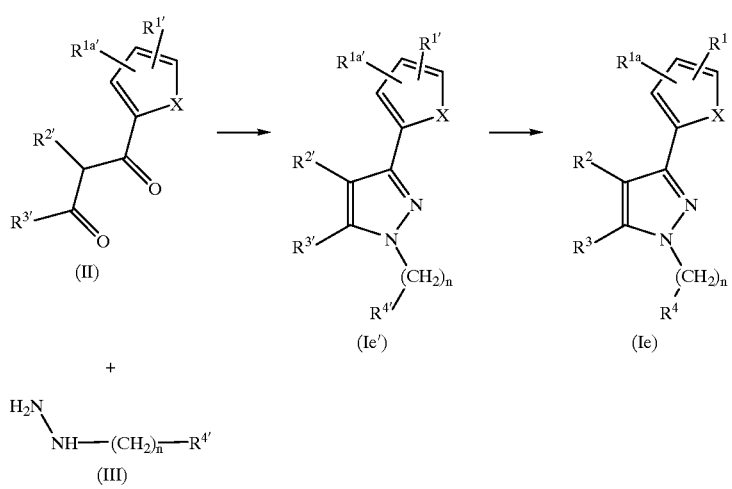

Thus, in the resulting compounds of the formula Ie, X, $R^1$, $R^{1a}$, $R^2$, $R^3$, $R^4$ and n have the meanings given above for the formula I, but $R^2$ and $R^3$ together with the carbon atoms which carry them may not form a benzene ring, i.e., $R^2$ and $R^3$ are hydrogen or an unsubstituted or substituted alkyl radical, aryl radical, arylalkyl radical, cycloalkyl radical, If free hydrazines of the formula IIII are employed, it is in many cases particularly advantageous to carry out the reaction with the dicarbonyl compounds of the formula IIunder acid catalysis. Suitable catalysts are, for example, organic carboxylic acids and sulfonic acids, such as acetic acid, trifluoroacetic acid, methanesulfonic acid or p- toluene-sulfonic acid, inorganic acids, such as hydrogen chloride, sulfuric acid or phosphoric acid, acidic salts, such as ammonium salts or hydrogen phosphates, or acidic ion exchangers. It may also be favorable to set a certain pH, or to operate in the presence of a buffer system. It is also possible to liberate the dicarbonyl compound of the formula II from a precursor, for example an acetal or ketal, using an acid catalyst, i.e., the dicarbonyl compound can be employed in the form of such a precursor. Preference is given to carrying out the reaction of compounds of the formula II with free hydrazines of the formula III in the presence of acetic acid.

The type and the amount of an added acid catalyst is determined by the individual case and depends, for example, on the reactivity of the reactants, the solvent or the intended temperature. If, for example, an acid such as acetic acid is used, this can act both as solvent and as catalyst, depending on the amount employed. If an acid addition salt of a hydrazine, for example an $R^4$—$(CH_2)$,-substituted hydrazinium chloride or hydrazinium sulfate, is employed instead of a free hydrazine, an acidic compound, which may act catalytically, is already introduced into the reaction mixture in this manner. If a hydrazinium salt is used, it is in many cases advantageous to buffer a part of the acid which has been introduced by addition of a certain amount of a base, for example by addition of sodium acetate or another buffering substance to the reaction mixture, to set a favorable pH.

The ratio at which the compounds of the formulae II and III are advantageously employed for the reaction depends on the individual case. The ratio may be approximately 1:1, but it is also possible to employ a reactant in a relatively low amount or a relatively large excess. If, for example, a reactant is prepared with great expense in a multi-step synthesis and the other reactant is easily obtained, it may be favorable, in order to make as much use as possible of the former, to employ the latter in excess, for example in 1.1- to 5-times the molar amount of the former.

In the reaction of the compounds of the formulae II and III to give the compound of the formula Ie', it may be possible that initially, as intermediate, the hydrazone of the formula IV is formed in which the radicals and n have the meanings given above for the formulae II and III and which may be isolable, depending on the reaction conditions used. Depending on the individual case, it may be advantageous, by the choice of the reaction conditions such as solvent, temperature and catalyst, to carry out the reaction in such a manner that it initially only proceeds to the hydrazone of the formula IV, which is then cyclized in a separate step to give the pyrazole of the formula Ie'. However, it may also be advantageous to carry out the reaction in such a manner that the pyrazole is formed directly. If the reaction is carried out in two steps, the hydrazone of the formula IV may, for cyclization, be isolated in substance, or the reaction mixture of the hydrazone preparation may be used and the cyclization may be effected for example by raising the temperature and/or by addition of a catalyst.

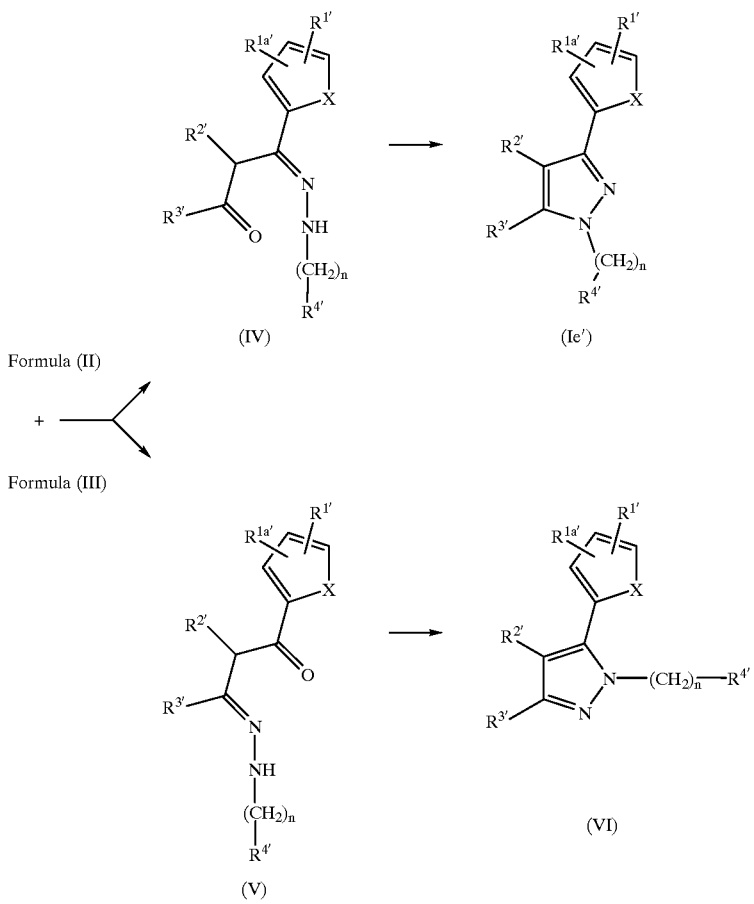

Depending on the reaction conditions and the reactivities of the reactants, the NH$_2$ group of the hydrazine of the formula III may, instead of with the carbonyl group which is adjacent to the heterocycle in the formula II, also react with the carbonyl group which is adjacent to the radical R$^3$. In this case, the reaction may also lead to the unwanted isomeric pyrazole of the formula VI, it being again possible that initially a hydrazone of the formula V is formed as intermediate which, if appropriate, may be isolated. In the formulae V and VI, the radicals and n have the meanings given above for the formulae II and III. If the reaction of the compounds of the formulae II and III yields mixtures of the isomeric pyrazoles Ie' and VI, these can be separated into the components by customary methods, for example by recrystallization or, in particular, by chromatography. A separation of an isomer mixture can also be carried out at the stage of the hydrazones.

Compounds of the formula I according to the invention in which the radicals R$^2$ and R$^3$ together with the carbon atoms which carry them form a benzene ring, i.e., compounds of the formula Ia, can be prepared by reacting compounds of the formula VII with hydrazines of the formula III or salts thereof. In the formulae VII, VIII and Ia', the radicals X, R$^{1'}$, R$^{1a'}$, R$^{4'}$, R$^{5'}$ and the number n may have the abovementioned meanings of X, R$^1$, R$^{1a}$, R$^4$, R$^5$ and n, but it is also possible that functional groups in these radicals are present in protected form or in the form of precursors. In the formulae Ia', VII and VIII, y has the abovementioned meanings, i.e. y may here be 0, 1, 2, 3 or 4. Z$^1$ in the formulae VII and VIII is a leaving group, for example halogen, or another suitable group, such as the trifluoromethanesulfonyloxy radical. Z$^1$ is preferably fluorine. If appropriate, compounds of the formula Ia according to the invention may then be obtained from the compounds of the formula Ia' by converting, in a subsequent reaction step, the groups which are present in protected form or in the form of precursors into the desired functional groups mentioned in the above definitions of R$^1$, R$^{1a}$, R$^4$ and R$^5$.

As in the reaction of compounds of the formulae II and III, in the reaction of compounds of the formulae VII and III a hydrazone may likewise be initially formed as intermediate, i.e., a compound of the formula VIII which may be isolable, depending on the reactivity of the starting materials used and the reaction conditions. Depending on the individual case, it may be advantageous to carry out the reaction of the compounds of the formulae III and VII by the choice of the reaction conditions such as solvents, temperature and catalyst in such a manner that it initially only leads to the hydrazone of the formulae VIII, and to cyclize this in a separate step to the indazole of the formula Ia'; however, it may also be favorable to carry out the reaction in such a manner that the indazole is formed directly.

In other cases, it may be suitable, owing to the reactivities of the starting materials, to carry out the reaction in two steps and to change the reaction conditions in the second step, the cyclization of the hydrazone of the formula VIII to the indazole of the formula Ia'. Thus, for example, if the group Z$^1$ in the compound of the formula VII or the formula VIII is not activated by substituents on the benzene ring, it is generally advantageous to condense initially the compounds of the formulae VII and III in the presence of an acid catalyst to give the hydrazone of the formula VIII, and to carry out the cyclization in a second step by operating in the presence of a base which increases the nucleophilicity of the β-nitrogen atom in the hydrazone grouping. If the reaction is carried out in two steps, the hydrazone of the formula VIII may be isolated in substance for the cyclization, or the reaction mixture of the hydrazone preparation may be employed for the cyclization without isolation of the hydrazone.

The above explanations for the reaction of the compounds of the formulae II and III with respect to solvents, reaction temperatures, catalysts, ratios, etc., apply correspondingly to the reaction of the compounds of the formulae VII and III. The reactions of compounds of the formula VII with the hydrazines of the formula III or salts thereof are likewise

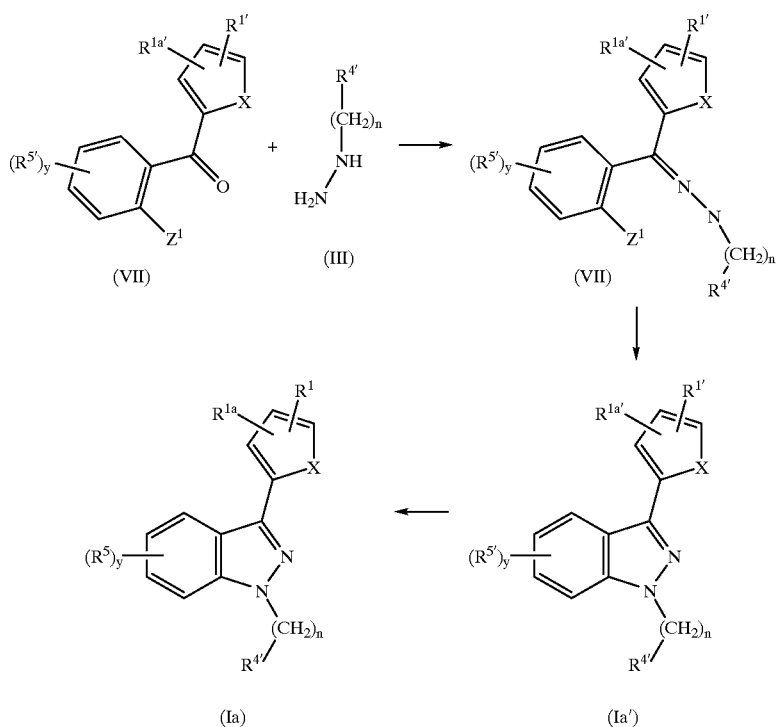

preferably carried out in a solvent or dispersant. Here, too, suitable solvents are, for example, water, alcohols, ethers, monoethers and diethers of ethylene glycol and of di- and triethylene glycol, esters, amides, nitrites, acids, sulfoxides and sulfones, hydrocarbons and chlorinated hydrocarbons. Examples of these solvents are given above. It is also possible to employ mixtures of two or more solvents. Here, too, preferred solvents are alcohols such as methanol and ethanol. Here, too, the reaction is generally carried out at temperatures from 0° C. to 150° C., preferably at temperatures from 20° C. to 130° C. The reaction is particularly preferably carried out under reflux at the boiling point of the solvent used, for example at the boiling point of methanol or ethanol.

If free hydrazines of the formula III are employed, it is in many cases particularly advantageous to carry out the reaction with the compounds of the formula VII under acidic catalysis. Once more, the above explanations apply here, too. Here, too, preference is given to carrying out the reaction of compounds of the formula VII with free hydrazines of the formula III in the presence of acetic acid. If an acid addition salt of a hydrazine is employed instead of a free hydrazine, it is again in many cases advantageous to buffer part of the acid that is introduced by addition of a certain amount of a base, for example by addition of sodium acetate, to set a favorable pH.

As already mentioned, the reaction of the compounds of the formulae VII and III can be interrupted at the stage of the hydrazone of the formula VIII. The cyclization of the hydrazone in a second step to give the indazole of the formula Ia', which constitutes a nucleophilic substitution of the group $Z^1$ on the aromatic by the β-nitrogen atom of the hydrazono group, can be carried out, depending on the reactivities given in the individual case, for example by heating in a solvent or dispersant. In many cases, addition of a base is advantageous. If the cyclization in the preparation of compounds of the formula Ia' is carried out in a separate step, this step is preferably carried out in the presence of a base. Suitable bases are, for example, hydroxides, carbonates, bicarbonates, hydrides, amides, alkoxides or organometallic compounds of alkali metals such as lithium, sodium, potassium or cesium or alkaline earth metals such as magnesium or calcium. Preferred bases are alkali metal alkoxides of $(C_1-C_4)$-alkanols such as sodium methoxide and potassium methoxide, sodium ethoxide and potassium ethoxide or sodium tert-butoxide and potassium tert-butoxide. It is also possible to employ mixtures of two or more bases. The base is preferably employed in an equimolar amount or in excess, usually in 1 to 3 times the molar amount of the compound of formula VIII.

Suitable solvents or dispersants for a cyclization of a hydrazone of the formula VIII to the indazole in a separate step are, for example, water, alcohols, ethers, monoethers and diethers of ethylene glycol and of di- and triethylene glycol, esters, amides, nitrites, sulfoxides, sulfones, hydrocarbons and chlorinated hydrocarbons. Examples of these solvents are given above. It is also possible to employ mixtures of two or more solvents. Preferred solvents for a cyclization in the presence of a base are aprotic solvents, in particular dipolar aprotic solvents, such as dimethylformamide, dimethylacetamide, hexamethylphosphoric triamide, N-methylpyrrolidone or dimethyl sulfoxide.

A cyclization of the hydrazone of the formula VIII in a separate step is generally carried out at temperatures from 0° C. to 150° C., preferably at temperatures from 20° C. to 130° C. Once more, particular preference is given to carrying out the cyclization under reflux at the boiling point of the solvent or solvent mixture used. Work-up can be carried out by standard methods.

A further process for preparing compounds of the formula Ia or Ia' is, in addition to the reaction of compounds of the formula VII with $R^{4'}$—$(CH_2)$n-substituted hydrazines of the formula III, the reaction of compounds of the formula VII with acylhydrazines of the formula IX. In the formula IX, R may, for example, be an alkyl radical, for example a $(C_1-C_4)$-alkyl radical, such as the methyl radical or the tert-butyl radical, or an aryl radical, for example a phenyl radical, which may be unsubstituted or substituted. An example of a suitable compound of the formula IX is benzhydrazide.

The reaction of the compounds of the formulae VII and IX can be carried out under the same conditions as mentioned above for the reaction of the compounds of the formulae VII and III. All of the above explanations apply here in a corresponding manner. The reaction of the compounds of the formulae VII and IX, which again can be carried out in one step or in two steps, initially leads to the acylhydrazones or acylindazoles which correspond to the formulae VIII or Ia' and contain, instead of the group $R^{4'}$—$(CH_2)$n, the group R—CO. After removal of the acyl group, these compounds give the indazoles of the formula X, in which X, $R^{1'}$, $R^{1a'}$, $R^{5'}$ and y have the meanings given above for the formulae Ia', VII and VIII.

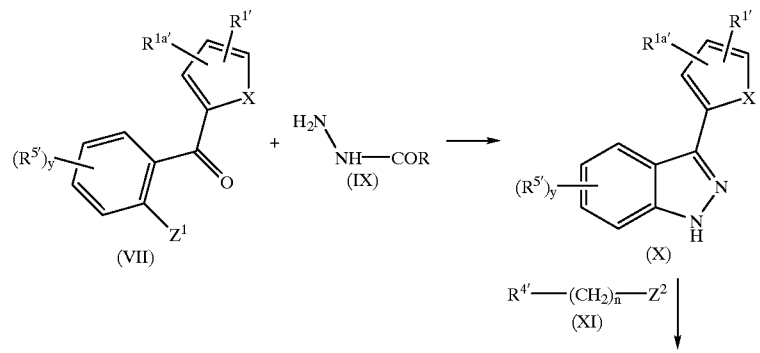

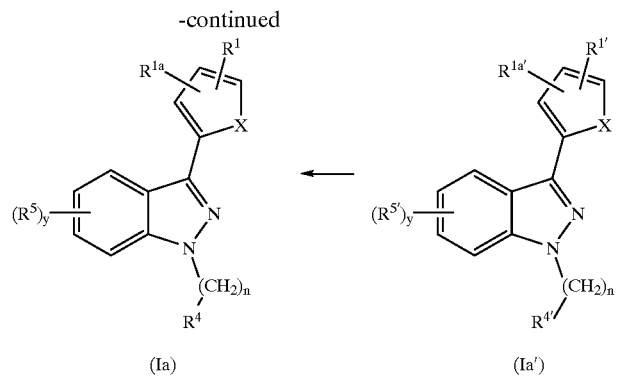

(Ia) (Ia')

For the removal of the acyl group, the acyl compounds may initially be isolated, but the removal can also be carried out in situ without their isolation. The acyl group can be removed, for example, in a customary manner by hydrolysis under acidic or basic conditions, for example using hydrochloric acid, sulfuric acid, phosphoric acid, lithium hydroxide, sodium hydroxide, sodium carbonate or potassium hydroxide. It can be carried out in water or in a water-containing organic solvent or dispersant. The reaction temperature and reaction time depend on the individual case, in general, the reaction is carried out from about room temperature to about 100° C. The indazoles of the formula X which are unsubstituted in the 1-position can be isolated by the customary methods or else be employed directly in a subsequent reaction.

The indazoles of the formula X can then be converted into the 1-substituted indazoles of the formula Ia' by reaction with alkylating agents of the formula XI. In the formula XI, $R^{4'}$ and n are as defined above, $Z^2$ is a leaving group, for example chlorine, bromine, iodine or a sulfonyloxy radical, such as methanesulfonyloxy, trifluoromethanesulfonyloxy, benzenesulfonyloxy or p-toluenesulfonyloxy. In general, the alkylating agent of the formula XI is employed in equimolar amounts or in excess, for example in 1 to 3 times the molar amount of the compound of formula X.

The alkylation of the compounds of the formula X can be carried out under the customary alkylation conditions. It is preferably carried out in a solvent or dispersant, for example in water, an alcohol, an ether, a monoether or diether of ethylene glycol or di- and triethylene glycol, a ketone, such as acetone or methyl ethyl ketone, an ester, an amide, a nitrile, a sulfoxide or sulfone, a hydrocarbon or a chlorinated hydrocarbon. The examples given above for these solvents also apply here. It is also possible to employ mixtures of two or more solvents, for example mixtures of an organic solvent with water. The alkylation is preferably carried out in water or in a dipolar aprotic solvent, for example dimethylformamide. The alkylation is generally carried out at temperatures from about 0° C. to about 150° C., preferably at temperatures from about 20 °C. to about 130° C. The alkylation is particularly preferably carried out under reflux at the boiling point of the solvent used.

The alkylation of the compounds of the formula X with the compounds of the formula XI is preferably carried out with addition of a base. Suitable bases are, for example, the hydroxides, carbonates, acetates, hydrides or alkoxides of alkali metals such as lithium, sodium or potassium or of alkaline earth metals such as magnesium or calcium. It is also possible to employ mixtures of bases. In general, the base is employed in equimolar amounts or in excess, for example in 1 to about 3 times the molar amount of the compound of formula X. Particularly preferably, the alkylation is carried out using potassium tert-butoxide or sodium hydride in dimethylformamide, or using sodium hydroxide in water. The work-up of the reaction mixture can be carried out by standard methods, and the product can be purified, if desired, by customary purification methods, for example by recrystallization or chromatography.

As already mentioned above, the radicals $R^{1'}$, $R^{1a'}$, $R^{2'}$, $R^{3'}$, $R^{4'}$ and $R^{5'}$ and also y in the compounds of the formulae Ia' and Ie' may have the meanings given in the definitions of $R^1$, $R^{1a}$, $R^2$, $R^3$, $R^4$ and $R^5$, so that the reaction products of the formulae Ia' and Ie' obtained by the illustrated synthesis processes already constitute compounds of the formulae Ia and Ie according to the invention. However, it is also possible to carry out multifarious structural modifications in the compounds of the formulae Ia' and Ie' obtained by the synthesis processes illustrated. As already mentioned, this may be the liberation of functional groups which were present in protected form during the synthesis.

However, it is also possible to introduce additional functional groups by customary chemical methods into compounds of the formulae Ia' and Ie' according to the invention, or to modify structural elements or functional groups which are present in compounds according to the invention by customary methods. These methods are known to the person skilled in the art and are described in detail in standard works, for example in Houben-Weyl, *Methoden der Organischen Chemie*, Thieme-Verlag, Stuttgart, or *Organic Reactions*, John Wiley & Sons, New York. A modification of reaction conditions to the reactivity of the compounds of the formulae Ia' and Ie' which may be necessary does not pose any problems to the person skilled in the art. The following reaction types may be mentioned as examples:

1. Hydrolysis of carboxylic esters to the carboxylic acids or the alcohols
2. Conversion of carboxylic acids into the carboxylic esters by esterification with alcohols in the presence of acid, conversion of carboxylic acids into carboxamides (which are aminocarbonyl compounds or carbamoyl compounds) or into carboxylic esters by in situ activation of the carboxylic acids and reaction with amines or alcohols or conversion of carboxylic acids into reactive derivatives, for example into the carbonyl chlorides, by reaction of the acids or salts thereof with chlorinating agents, such as thionyl chloride, oxalyl chloride or phosphorus halides, and reaction of the reactive derivatives with alcohols and amines to give carboxylic esters and carboxamides.
3. Conversion of sulfonic acids or salts thereof into the sulfonyl chlorides, for example with phosphorus halides, and reaction of the sulfonyl chlorides with amines to give sulfonamides.
4. Reduction of carboxylic acid derivatives to give aldehydes or alcohols and reduction of aldehydes and ketones to alcohols, and also addition of organometallic compounds, such as Grignard reagents or organolithium compounds, to carboxylic acid groups or aldehyde or ketone groups with formation of ketones or alcohols.

5. Oxidation of alcohols to aldehydes or ketones.
6. Etherification, halogenation and esterification of alcohols.
7. Reduction of nitro compounds to amines.
8. Acylation of amines to carboxamides with carboxylic acids in the presence of an activating agent or with reactive carboxylic acid derivatives, such as carbonyl chlorides, and reaction of amines with sulfonyl chlorides to give sulfonamides.
9. Nucleophilic substitutions at aliphatic carbon atoms, for example reaction of halogen compounds with amines or mercaptans.
10. Electrophilic aromatic substitution with replacement of a hydrogen atom at a carbocyclic or heterocyclic aromatic ring by a functional group, for example halogenation, amino methylation, formylation, acylation, sulfonation.

The starting materials of the formulae II and VII are known or can be prepared similarly to known compounds by well-known standard methods described in the literature. 1,3-dicarbonyl compounds of the formula II are obtainable, for example, by ester condensations or by acylations of β-ketoesters with subsequent removal of the ester group. The aromatics of the formula VII can be obtained, for example, by Friedel-Crafts acylations of furans, thiophenes and pyrroles with benzoic acid derivatives such as, for example, acyl chlorides. More details about these reactions can be found in the standard works such as *Houben-Weyl* or *Organic Reactions* (supra). The hydrazines of the formulae III and IX and the alkylating agents of the formula XI are also known, or they can be prepared by well-known processes, details of which can be found in these standard works.

The compounds of the formula I according to the invention effect an increase of the cGMP concentration via the activation of the sGC, and they are therefore useful agents for the therapy and prophylaxis of disorders which are associated with a low or decreased cGMP level or which are caused thereby, or for whose therapy or prophylaxis an increase of the present cGMP level is desired. The activation of the sGC by the compounds of the formula I can be examined, for example, in the activity assay described below, and their action on organs can be examined, for example, by the determination of the relaxation of rat aorta.

Disorders and pathological conditions which are associated with a low cGMP level or in which an increase of the cGMP level is desired and for whose therapy and prophylaxis it is possible to use compounds of the formula I are, for example, cardiovascular diseases, such as endothelial dysfunction, diastolic dysfunction, atherosclerosis, hypertension, stable and unstable angina pectoris, thromboses, restenoses, myocardial infarction, strokes, coronary insufficiency or pulmonary hypertonia, or, for example, erectile dysfunction, asthma bronchiale, chronic kidney insufficiency and diabetes. Compounds of the formula I can additionally be used in the therapy of cirrhosis of the liver and also, owing to their partially synergistic action with the retrograde messenger substance NO, for improving a restricted memory performance or ability to learn.

The compounds of the formula I and their physiologically acceptable salts can be administered to animals, preferably to mammals, and in particular to humans as pharmaceuticals by themselves, in mixtures with one another or in the form of pharmaceutical preparations. The present invention therefore also provides the compounds of the formula I and their physiologically acceptable salts for use as pharmaceuticals, their use for normalizing a disturbed cGMP balance and in particular their use in the therapy and prophylaxis of the abovementioned syndromes, and also their use for preparing medicaments for this purpose. Furthermore, the present invention provides pharmaceutical preparations which comprise as active component an effective dose of at least one compound of the formula I and/or a physiologically tolerable salt thereof, in addition to customary pharmaceutically acceptable carriers and additives.

The pharmaceuticals can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. However, administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

The pharmaceutical preparations usually comprise 0.5 to 90 percent by weight of the compounds of the formula I and/or their physiologically acceptable salts. The preparation of the pharmaceutical preparations can be carried out in a manner known per se. For this purpose, one or more compounds of the formula I and/or their physiologically acceptable salts, together with one or more solid or liquid pharmaceutical carriers and/or auxiliaries and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules, it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc.

Suitable carriers for the preparation of solutions, for example of solutions for injection, or of emulsions or syrups are, for example, water, saline, alcohols such as ethanol, glycerol, polyols, sucrose, invert sugar, glucose, mannitol, vegetable oils, etc. It is also possible to lyophilize the compounds of the formula I and their physiologically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical preparations can also contain customary additives, for example fillers, disintegrants, binders, lubricants, wetting agents, stabilizers, emulsifiers, dispersants, preservatives, sweeteners, colorants, flavorings or aromatizers, thickeners, diluents, buffer substances, furthermore solvents or solubilizers or agents for achieving a depot effect, and salts for altering the osmotic pressure, coating agents or antioxidants.

The dosage of the active compound of the formula I to be administered and/or of a physiologically acceptable salt thereof depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of the formula I.

In general, a daily dose of approximately 0.01 to about 100 mg/kg, preferably about 0.1 to about 10 mg/kg, in particular about 0.3 to about 5 mg/kg (in each case mg per kg of bodyweight) are appropriate for administration to an adult weighing approximately 75 kg in order to obtain effective results. The daily dose can be administered in a single dose or, in particular when larger amounts are administered, be divided into several, for example two, three or four individual doses. In some cases, depending on the individual response, it may be necessary to deviate upwards or downwards from the given daily dose. Pharmaceutical preparations normally contain about 0.2 to about 500 mg, preferably about 1 to about 200 mg, of active compound of the formula I and/or its physiologically acceptable salts per dose.

The compounds of the formula I activate the soluble guanylate cyclase. On account of this property, apart from use as pharmaceutically active compounds in human medicine and veterinary medicine, they can also be employed as a scientific tool or as aids for biochemical investigations in which such an effect on guanylate cyclase is intended, and also for diagnostic purposes, for example in the in vitro diagnosis of cell or tissue samples. The compounds of the formula I and salts thereof can furthermore be employed, as already mentioned above, as intermediates for the preparation of other pharmaceutically active compounds.

The following examples illustrate embodiments of the invention, without limiting the scope of the invention or its equivalents.

The abbreviations used in the description of the experiments are:

RT—Room temperature
THF—Tetrahydrofuran
DMF—Dimethylformamide

EXAMPLE 1

1-Benzyl-3-(5-carboxy-2-furyl)indazole, potassium salt (starting material)

1a) 5-(2-Fluorobenzoyl)furan-2-carboxylic acid: 132.6 g (0.53 mol) of methyl 5-(2-fluorobenzoyl)furan-2-carboxylate were introduced into a solution of 31.47 g (0.56 mol) of potassium hydroxide in 350 ml of water, and the mixture was heated to 70° C. After 1 h, the solution was filtered and acidified with conc. hydrochloric acid. The precipitate was filtered off with suction and recrystallized from ethanol. This gave 106.3 g (85%) of the title compound. m.p.: 195–196° C.

1b) 1-Benzyl-3-(5-carboxy-2-furyl)indazole, potassium salt: 70.26 g (0.3 mol) of 5-(2-fluorobenzoyl)furan-2-carboxylic acid were initially charged in 350 ml of methanol, 109.95 g (0.9 mol) of benzylhydrazine were added and the mixture was, after addition of 8 ml of glacial acetic acid, heated under reflux for 6 h. For work-up, the mixture was concentrated using a rotary evaporator, the residue was taken up in 2N aqueous sodium hydroxide solution and extracted with ethyl acetate. The aqueous phase was acidified with 2N hydrochloric acid and extracted with ethyl acetate. The residue that remained after drying and concentration using a rotary evaporator was recrystallized from ethyl acetate/n-hexane. The 68.3 g (0.20 mol) of 5-(2-fluorobenzoyl)furan-2-carboxylic acid benzylhydrazone (m.p.: 147° C. (decomp.)) obtained in this manner were dissolved in 400 ml of DMF, 45.38 g (0.40 mol) of potassium tert-butoxide were introduced and the mixture was heated under reflux for 30 minutes. The precipitate was filtered off with suction, washed with dichloromethane and recrystallized from ethanol/water (95:5). This gave 57.7 g (54%) of the title compound. The corresponding cyclization of the precursor which was still contained in the mother liquor gave 25.9 g of product. m.p.: >300 ° C. $^1$H-NMR ($D_6$-DMSO): δ=5.73 (s, 2H, $CH_2$), 6.68 (d, 1H, H-3'), 6.92 (d, 1H, H-4'), 7.18-7.38 (m, 6H, phenyl-H, H-5), 7.45 (t, 1H, H-6), 7.75 (d, 1H, H-7), 8.18 (d, 1 H, H-4)

EXAMPLE 2

1-Benzyl-3-(5-ethoxycarbonyl-2-furyl)indazole (starting material): 52.4 g (0.15 mol) of 1-benzyl-3-(5-carboxy-2-furyl)indazole, potassium salt, were initially charged in 1250 ml of toluene, and after addition of 200 ml of abs. ethanol and 50 ml of conc. sulfuric acid the mixture was stirred under reflux on a water separator. After 3 hours, the mixture was concentrated using a rotary evaporator, the oil that remained was taken up in water/ethyl acetate and the aqueous phase was separated off. The organic phase was washed with water and 7.5% strength $NaHCO_3$ solution, dried with sodium sulfate and concentrated. The residue was recrystallized from isopropanol. This gave 37.8 g (73%) of the title compound. m.p.: 98–99 ° C.

EXAMPLE 3

1-Benzyl-3-(5-hydroxymethyl-2-furyl)indazole (starting material): 2.06 g (54.6 mmol) of lithium aluminum hydride were initially charged in 250 ml of absolute THF, and a solution of 18.8 g (54.6 mmol) of 1-benzyl-3-(5-ethoxycarbonyl-2-furyl)indazole in 250 ml of THF was added dropwise. After 45 min the mixture was admixed with 25% strength potassium carbonate solution and stirred at RT for 30 min and the precipitate was filtered off with suction and washed with THF. The combined organic phases were concentrated using a rotary evaporator and the residue was recrystallized from isopropanol. This gave 11.0 g (67%) of the title compound. m.p.: 113–114° C.

The following compounds were prepared correspondingly:

EXAMPLE 4

3-(5–Carboxy-2-furyl)-1-(3,5-bis(trifluoromethyl)phenyl)indazole m.p.: 256–257° C.

EXAMPLE 5

3-(5-Ethoxycarbonyl-2-furyl)-1-(3,5-bis(trifluoromethyl)phenyl)indazole m.p.: 128–129° C.

EXAMPLE 6

3-(5-Hydroxymethyl-2-furyl)-1-(3,5-bis(trifluoromethyl)phenyl)indazole m.p.: 136–138° C.

EXAMPLE 7

5-Benzyl-3-(5-((2-hydroxyethoxy)carbonyl)-2-furyl)indazole: 200 mg (0.6 mmol) of 1-benzyl-3-(5-ethoxycarbonyl-2-furyl)indazole were dissolved in ethylene glycol and heated under reflux for 1.5 h. For work-up, the mixture was concentrated using a rotary evaporator and the crude product was chromatographed over silica gel using hexane/ethyl acetate (1:1). This gave 68 mg (31%) of the title compound. $^1$H-NMR ($D_6$-DMSO): δ=3.72 (q, 2H, $CH_2$—OH), 4.31 (t, 2H, $CH_2$–C—OH), 4.93 (t, 1H, OH), 6.78 (s, 2H, $CH_2$-phenyl), 7.23 (d, 1H, H-3'), 7.23-7.40 (m, 6H, phenyl-H, H-5), 7.50 (d, 1H, H-4'), 7.50 (t, 1H, H-6), 7.83 (d, 1H, H-7), 8.16 (d, 1H, H-4).

EXAMPLE 8

1-Benzyl-3-(5-methoxycarbonyl-2-furyl)-5-nitroindazole

8a) Methyl 5-(2-fluoro-5-nitrobenzoyl)furan-2-carboxylate: A solution of 24.7 g (0.2 mol) of methyl furan-2-carboxylate in 50 ml of dried carbon tetrachloride was added dropwise to a suspension of 2 g of iron(III) chloride and 29.0 g (0.14 mol) of 2-fluoro-5-nitrobenzoyl chloride in 100 ml of dried carbon tetrachloride, and the mixture was heated under reflux (80° C.) for 14 h. 50 ml of methanol were subsequently added, the mixture was stirred at RT for 30 min and concentrated using a rotary evaporator. The residue that remained was taken up in ethyl acetate, washed with water and $NaHCO_3$ solution, dried with sodium sulfate, concentrated using a rotary evaporator and recrystallized from isopropanol. This gave 3.5 g (9%) of the title compound. m.p.: 134–135° C.

8b) 1-Benzyl-3-(5-methoxycarbonyl-2-furyl)-5-nitroindazole: 2.6 g (9 mmol) of methyl-5-(2-fluoro-5-nitrobenzoyl)furan-2-carboxylate and 3.31 g (27 mmol) of benzylhydrazine were initially charged in approximately 60 ml of methanol and, after addition of 0.2 ml of glacial acetic acid, heated to reflux for 15 min. The precipitate was filtered off with suction, washed with a little methanol and dried at RT in a vacuum drying cabinet. The crude product was purified by silica gel chromatography using dichloromethane. This gave 2.9 g (85%) of the title compound. m.p.: 171–173° C.

EXAMPLE 9

5-Amino-1-benzyl-3-(5-methoxycarbonyl-2-furyl)indazole: 0.9 g (2.4 mmol) of 1-benzyl-3-(5-methoxycarbonyl-2-furyl)-5-nitroindazole were dissolved in 100 ml of methanol/THF (1:1) by gentle warming, a solution of 2.5 g (14.4 mmol) of sodium dithionite in 50 ml of water was added and the mixture was stirred at RT for 16 h. For work-up, the mixture was concentrated and the residue was chromatographed over silica gel using dichloromethane/methanol (98.5:1.5). This gave 140 mg (17%) of the title compound. m.p.: 195–196° C.

EXAMPLE 10

5-Amino-1-benzyl-3-(5-hydroxymethyl-2-furyl)indazole: A solution of 80 mg (0.23 mmol) of 5-amino-I-benzyl-3-(5-methoxycarbonyl-2-furyl)indazole in 5 ml of THF was added dropwise to 0.01 g (0.3 mmol) of lithium aluminum hydride in 5 ml of THF, and the mixture was stirred at RT. After 3 h, 10 ml of a 25% strength $K_2CO_3$ solution were added and stirring was continued for 30 min. The precipitate was filtered off with suction and extracted with boiling THF, the combined organic phases were dried and concentrated and the residue was chromatographed over silica gel using 95:5 dichloromethane/methanol. This gave 21 mg (29%) of the title compound. m.p.: 156° C.

EXAMPLE 11

1-Benzyl-3-(5-carboxy-2-furyl)-6-nitroindazole

11a) Methyl 5-(2-fluoro-4-nitrobenzoyl)furan-2-carboxylate: 8.4 g of iron(III) chloride, 44.8 g (0.22 mol) of 2-fluoro-4-nitrobenzoyl chloride and 33.4 g (0.26 mol) of methyl furan-2-carboxylate in 80 ml of carbon tetrachloride were heated under reflux for 2 days. For work-up, 100 ml of methanol were added, the mixture was stirred for 10 min and then concentrated, the residue was taken up in ethyl acetate/water and the organic phase was extracted repeatedly with $Na_2CO_3$ solution. The residue that remained after drying and concentration of the ethyl acetate phase was extracted with methanol, and the insoluble fraction was chromatographed over silica gel using dichloromethane. This gave 19.0 g (29%) of the title compound. m.p.: 136–138° C.

11b) 5-(2-Fluoro-4-nitrobenzoyl)furan-2-carboxylic acid: 14.5 g (49 mmol) of methyl 5-(2-fluoro-4-nitrobenzoyl)furan-2-carboxylate were added to 200 ml of 0.1N aqueous sodium hydroxide solution, and the mixture was stirred at RT for 3 days. The mixture was subsequently adjusted to pH 4 using 1N hydrochloric acid, cooled in an ice bath for 30 min and filtered off with suction. This gave 8.6 g (62%) of the title compound. m.p.: 170° C. (decomp).

$^1$H-NMR ($D_6$-DMSO): δ=7.39 (d, 1H, H-4'), 7.50 (d, 1H, H-3'), 8.00 (dd, 1H, H-6), 8.25 (dd, 1H, H-5), 8.34 (dd, 1H, H-3)

11c) 1-Benzyl-3-(5-carboxy-2-furyl)-6-nitroindazole: 8.5 g (30 mmol) of 5-(2-fluoro-4-nitrobenzoyl)furan-2-carboxylic acid were dissolved in 100 ml of methanol and admixed with 11.2 g (91 mmol) of benzylhydrazine, and the mixture was heated under reflux for 7 h. The mixture was subsequently poured into water, adjusted to pH 4 using conc. hydrochloric acid and extracted with ethyl acetate. The combined organic phases were dried and concentrated. For cyclization, the crude intermediate was dissolved in 50 ml of DMF, 6.8 g (61 mmol) of potassium tert-butoxide were added and the mixture was heated under reflux for 3 h. For work-up, the mixture was concentrated, adjusted to pH 4 using 1N hydrochloric acid and extracted with ethyl acetate, the organic phase was concentrated and the residue was chromatographed over silica gel using ethyl acetatelglacial acetic acid (60:1). This gave 8 g (approximately 73%) of the title compound as an oil.

$^1$H-NMR ($D_6$-DMSO): δ=5.96 (s, 2H, $CH_2$), 7.22–7.41 (m, 7H, phenyl-H, H-3', H-4'), 8.13 (dd, 1H, H-5), 8.38 (d, 1H, H-4), 8.93 (d, 1H, H-7)

EXAMPLE 12

3-(5–Carboxy-2-furyl)-1-(2-phenylethyl)indazole: 5 g (21 mmol) of 5-(2-fluorobenzoyl)furan-2-carboxylic acid, 12 g (51 mmol) of (2-phenylethyl)hydrazinium sulfate and 8.4 g (102 mmol) of sodium acetate in 50 ml of ethanol were boiled under reflux for 12 h. The mixture was subsequently concentrated and stirred with water/ethyl acetate, and the ethyl acetate phase was separated off, dried and concentrated. For purification, the crude intermediate (hydrazone) was chromatographed over silica gel using dichloromethane/methanol (9:1). 4 g (11.3 mmol) of the hydrazone were dissolved in 20 ml of DMF and, with 2.5 g (23 mmol) of potassium tert-butoxide, heated under reflux for 3 h. The precipitated potassium salt of the title acid was filtered off with suction. The concentrated filtrate was chromatographed over silica gel using dichloromethane/methanol (7:3). This gave a total of 1.9 g (27%, calculated for the acid) of the title compound. 3-(5-carboxy-2-furyl)indazole was formed as a byproduct. m.p.: decomp. >190° C.

$^1$H-NMR ($D_6$-DMSO): δ=3.20 (t, 2H, $CH_2$-phenyl), 4.65 (t, 2H, $CH_2$-N), 7.00 (m, 2H, H-3', H-4'), 7.13-7.23 (m, 6H, phenyl-H, H-5), 7.38 (t, 1H, H-6), 7.60 (d, 1H, H-7), 8.14 (d, 1H, H-4)

EXAMPLE 13

3-(5-Ethoxycarbonyl-2-furyl)-1-(2-phenylethyl)indazole: 0.8 g (2.4 mmol) of 3-(5-carboxy-2-furyl)-1-(2-phenylethyl)indazole were admixed with 25 ml of ethanol, 150 ml of toluene and 2 ml of conc. sulfuric acid and heated on a water separator for 3 h. Silica gel chromatography using dichloromethanelhexane (2:1) of the residue that was obtained after concentration using a rotary evaporator gave 400 mg (46%) of the title compound.

$^1$H-NMR ($D_6$-DMSO): δ=1.40 (t, 3H, $CH_3$), 3.34 (t, 2H, $CH_2$-phenyl), 4.35 (q, 2H, $OCH_2$), 4.73 (t, 2H, $CH_2$-N), 7.08-7.37 (m, 6H, phenyl-H, H-3'), 7.38 (t, 1H, H-5), 7.45 (t, 1H, H-6), 7.48 (d, 1H, H-4'), 7.65 (d, 1H, H-7), 8.10 (d, 1H, H-4)

EXAMPLE 14

3-(5-Hydroxymethyl-2-furyl)-1-(2-phenylethyl)indazole: A solution of 300 mg (0.83 mmol) of 3-(5-ethoxycarbonyl-2-furyl)-1-(2-phenylethyl)indazole in 10 ml of THF was added dropwise to 31.5 mg (0.83 mmol) of lithium aluminum hydride in 10 ml of THF. After 1 h, the mixture was admixed with 25% strength potassium carbonate solution and the precipitate was separated off and washed with THF. The combined THF filtrates were dried and concentrated. The crude product was purified by silica gel chromatography using dichloromethane/methanol (95:5). This gave 200 mg (75%) of the title compound.

$^1$H-NMR (D$_6$-DMSO): δ=3.20 (t, 2H, CH$_2$-phenyl ), 4.53 (bs, 2H, CH$_2$O), 4.66 (t, 2H, CH$_2$-N), 6.50 (d, 1H, H-3'), 6.98 (d, 1H, H-4'), 7.15-7.27 (m, 6H, phenyl-H, H-5), 7.38 (t, 1H, H-6), 7.58 (d, 1H, H-7), 8.08 (d, 1H, H-4)

EXAMPLE 15

3-(5–Carboxy-2-furyl)indazole: 2.5 g (11 mmol) of 5-(2-fluorobenzoyl)furan-2-carboxylic acid, 3.28 g (24 mmol) of benzhydrazide and 2 drops of glacial acetic acid in 50 ml of ethanol were heated under reflux for 10 h. The mixture was subsequently concentrated using a rotary evaporator and the residue was taken up in water, made alkaline using 2 N NaHCO$_3$ solution and extracted with ethyl acetate. The aqueous phase was made acidic using 2N hydrochloric acid and extracted with ethyl acetate. The combined organic phases were dried and concentrated using a rotary evaporator. The residue was dissolved in 25 ml of THF, 2.74 g (24.2 mmol) of potassium tert-butoxide were added and the mixture was stirred at reflux temperature for 1.5 h. After cooling, the mixture was concentrated using a rotary evaporator and the residue was taken up in 1 N aqueous sodium hydroxide solution and extracted with ethyl acetate. The precipitate that resulted when the aqueous phase was acidified was filtered off with suction, washed with water and dried in a vacuum drying cabinet at 40° C. This gave 1.88 g (75%) of the title compound. m.p.: 205° C. (decomp).

$^1$H-NMR (D$_6$-DMSO): δ=7.15 (d, 1H, H-3'), 7.28 (t, 1H, H-5), 7.40 (d, 1H, H-4'), 7.48 (t, 1H, H-6), 7.63 (d, 1H, H-7), 8.15 (d, 1H, H-4), 13.1 (bs, 1H, COOH), 13.54 (bs, 1H, H-1)

EXAMPLE 16

3-(5-Ethoxycarbonyl-2-furyl)indazole: 1.75 g (7.7 mmol) of 3-(5-carboxy-2-furyl)indazole together with 2.5 ml of concentrated sulfuric acid in 60 ml of toluene and 20 ml of ethanol were heated on a water separator. Customary work-up gave 1.2 g (60%) of the title compound.

$^1$H-NMR (D$_6$-DMSO): δ=1.36 (t, 3H, CH$_3$), 4.35 (q, 2H, CH$_2$), 7.10 (d, 1H, H-3'), 7.30 (t, 1H, H-5), 7.44 (t, 1H, H-6), 7.46 (d, 1H, H-4'), 7.64 (d, 1H, H-7), 8.13 (d, 1H, H-4), 13.60 (bs, 1 H, H-1)

EXAMPLE 17

1-((5-Chloro-2-thienyl)methyl)-3-(5-ethoxycarbonyl-2-furyl)indazole: 600 mg (2.3 mmol) of 3-(5-ethoxycarbonyl-2-furyl)indazole together with 265 mg (2.4 mmol) of potassium tert-butoxide were initially charged in 10 ml of DMF, 430 mg (2.6 mmol) of 2-chloro-5-(chloromethyl)thiophene in 1 ml of DMF were added dropwise and the mixture was stirred at RT for 2 h. Customary work-up gave 350 mg (41%) of the title compound. m.p.: 124–126° C.

EXAMPLE 18

1-((5-Chloro-2-thienyl)methyl)-3-(5-hydroxymethyl-2-furyl)indazole: The compound was prepared similarly to Example 14 from 1-((5-chloro-2-thienyl)methyl)-3-(5-ethoxycarbonyl-2-furyl)indazole by reduction with lithium aluminum hydride.

1H-NMR (D$_6$-DMSO): δ=4.50 (d, 2H, CH$_2$O), 5.35 (t, 1H, OH), 5.88 (s, 2H, N-CH$_2$), 6.48 (d, 1H, thiophene-H-3), 6.98 (m, 2H, H-3', thiophene-H-4), 7.26 (t, 1H, H-5), 7.41 (d, 1H, H-4'), 7.48 (t, 1H, H-6), 7.81 (d,$_1$ H, H-7), 8.10 (d, 1H, H-4)

EXAMPLE 19

1-Benzyl-3-(5-chlorocarbonyl-2-furyl)indazole: 15 g (0.05 mol) of 1-benzyl-3-(5-carboxy-2-furyl)indazole and 36.43 g (0.31 mol) of thionyl chloride in 400 ml of benzene were heated under reflux for 3 h. The cooled mixture was filtered and concentrated. This gave 11.95 g (approximately 76%) of the title compound which was used for subsequent reactions without any further purification.

EXAMPLE 20

1-Benzyl-3-(5-(N-(4-trifluoromethylphenyl)carbamoyl)-2-furyl)indazole: 0.29 g (1.8 mmol) of 4-trifluoromethylaniline were initially charged in 20 ml of THF$_1$ 0.14 g (1.8 mmol) of pyridine were added and a solution of 0.5 g (1.5 mmol) of 1-benzyl-3-(5-chlorocarbonyl-2-furyl)indazole in 10 ml of THF was added dropwise at RT. After 0.5 h, the mixture was poured into ice-water and the precipitate was filtered off with suction and recrystallized from isopropanol. This gave 0.47 g (69%) of the title compound. m.p.: 205–206° C.

Using processes similar to Example 20, the following compounds were obtained:

EXAMPLE 21

1-Benzyl-3-(5-(N-phenylcarbamoyl)-2-furyl)indazole m.p.: 138–143° C.

EXAMPLE 22

1-Benzyl-3-(5-(N-(4-chlorophenyl )carbamoyl)-2-furyl)indazole m.p.: 202–205° C.

EXAMPLE 23

1-Benzyl-3-(5-(N-(4-nitrophenyl)carbamoyl)-2-furyl)indazole m.p.: 204–208° C.

EXAMPLE 24

1-Benzyl-3-(5-(N-(2-naphthyl)carbamoyl)-2-furyl)indazole m.p.: 167° C.

EXAMPLE 25

1-Benzyl-3-(5-(N-(2-thiazolyl)carbamoyl)-2-furyl)indazole m.p.: 167–168° C.

EXAMPLE 26

1-Benzyl-3-(5-(N-(benzyloxy)carbamoyl)-2-furyl)indazole m.p.: 140–143° C.

EXAMPLE 27

1-Benzyl-3-(5-(N-methyl-N-phenylcarbamoyl)-2-furyl)indazole m.p.: 190° C.

EXAMPLE 28

1-Benzyl-3-(5-(N-(4-methoxyphenyl)carbamoyl)-2-furyl)indazole m.p.: 175° C.

EXAMPLE 29

1-Benzyl-3-(5-(N-(2-hydroxyphenyl)carbamoyl)-2-furyl)indazole m.p.: 196–197° C.

EXAMPLE 30

1-Benzyl-3-(5-(N-(2-hydroxyethyl)carbamoyl)-2-furyl)indazole: 0.23 g (3.7 mmol) of ethanolamine were initially charged in 20 ml of THF and a solution of 0.5 g (1.5 mmol) of 1-benzyl-3-(5-chlorocarbonyl-2-furyl)indazole in 10 ml of THF was added dropwise. After 0.75 h, the mixture was poured into ice-water and the precipitate was filtered off with suction and recrystallized from ethyl acetate. This gave 0.33 g (62%) of the title compound. m.p.: 119–127° C.

Using processes similar to Example 30, the following compounds were obtained:

EXAMPLE 31

1-Benzyl-3-(5-(N-isopropylcarbamoyl)-2-furyl)indazole m.p.: 156° C.

EXAMPLE 32

1-Benzyl-3-(5-(N-(n-propyl)carbamoyl)-2-furyl)indazole m.p.: 152° C.

EXAMPLE 33

1-Benzyl-3-(5-(N-cyclohexylcarbamoyl)-2-furyl)indazole m.p.: 165° 0 C.

EXAMPLE 34

1-Benzyl-3-(5-(N-benzylcarbamoyl)-2-furyl)indazole m.p.: 113–124° C.

EXAMPLE 35

1-Benzyl-3-(5-(N-(2-dimethylaminoethyl)carbamoyl)-2-furyl)indazole m.p.: 130° 0 C.

EXAMPLE 36

1-Benzyl-3-(5-(N-(2-diisopropylaminoethyl)carbamoyl)-2-furyl)indazole m.p.: 119–127° C.

EXAMPLE 37

1-Benzyl-3-(5-(N-(carbamoylmethyl)carbamoyl)-2-furyl)indazole m.p.: 219–222° C.

EXAMPLE 38

1-Benzyl-3-(5-(N-(2-pyridylmethyl)carbamoyl)-2-furyl)indazole m.p.: 160° C.

EXAMPLE 39

1-Benzyl-3-(5-carbamoyl-2-furyl)indazole: With simultaneous introduction of ammonia, a solution of 0.8 g (2.4 mmol) of 1-benzyl-3-(5-chlorocarbonyl-2-furyl)indazole in 10 ml of THF was added dropwise to 25 ml of a saturated solution of ammonia in THF. After 45 min, the mixture was poured into ice-water and extracted with ethyl acetate, and the organic phase was washed with 1N hydrochloric acid, dried and concentrated using a rotary evaporator. The crude product was recrystallized from isopropanol. This gave 0.29 g (38%) of the title compound. m.p.: 259° C.

EXAMPLE 40

1-Benzyl-3-(5-(N-methylcarbamoyl)-2-furyl)indazole: 2.97 ml (5.94 mmol) of a 2M solution of methylamine in THF were initially charged in 20 ml of THF, and a solution of 0.8 g (2.4 mmol) of 1-benzyl-3-(5-chlorocarbonyl-2-furyl)indazole in 10 ml of THF was added dropwise at RT. After 1 h, the mixture was poured into ice-water and the oil that separated off was extracted with ethyl acetate. The organic phase was washed with 1N hydrochloric acid, dried and concentrated using a rotary evaporator. The crude product was recrystallized from isopropanol. This gave 0.44 g (55%) of the title compound. m.p.: 182–183° C.

EXAMPLE 41

1-Benzyl-3-(5-formyl-2-furyl)indazole: 7.7 g (25.3 mmol) of 1-benzyl-3-(5-hydroxymethyl-2-furyl)indazole and 11 g (126.5 mmol) of activated manganese(IV) oxide in 200 ml of dry carbon tetrachloride were stirred under reflux for 4.5 h. For work-up, the mixture was filtered off with suction and the filtrate was washed with water, dried and concentrated using a rotary evaporator. The crude product was recrystallized from isopropanol. This gave 4.8 g (63%) of the title compound. m.p.: 108° C.

EXAMPLE 42

1-Benzyl-3-(5-(1-hydroxypropyl)-2-furyl)indazole: At 10° C., 1.1 ml (1.1 mmol) of a 1M solution of ethylmagnesium bromide in THF were added dropwise to 300 mg (0.99 mmol) of 1-benzyl-3-(5-formyl-2-furyl)indazole in 20 ml of diethyl ether. After 1 h at 10° C., the mixture was poured into ice-water and extracted with ethyl acetate, dried and concentrated. The crude product was purified by silica gel chromatography using dichloromethane/methanol (95:5). This gave 200 mg (61%) of the title compound.

$^1$H-NMR (D$_6$-DMSO): δ=0.95 (t, 3H, CH$_3$),1.80 (m, 2H, CH$_2$-C—O), 4.55 (m, 1H, CH—O), 5.36 (bs, 1H, OH), 5.78 (s, 2H, CH$_2$-phenyl), 6.43 (d, 1 H, H-3'), 6.94 (d, 1H, H-4'), 7.20-7.38 (m, 6H, phenyl-H, H-5), 7.45 (t, 1H, H-6), 7.75 (d, 1H, H-7), 8.12 (d, 1H, H-4)

Using processes similar to Example 42, the following compounds were obtained:

EXAMPLE 43

1-Benzyl-3-(5-(1-hydroxy-1-phenylmethyl)-2-furyl)indazole m.p.: 138–139° C.

EXAMPLE 44

1-Benzyl-3-(5-(1-hydroxyprop-2-in-1-yl)-2-furyl)indazole m.p.: 151° C.

EXAMPLE 45

1-Benzyl-3-(5-(1-hydroxy-1-methylethyl)-2-furyl)indazole: 3.0 g (8.7 mmol) of 1-benzyl-3-(5-ethoxycarbonyl-2-furyl)indazole were dissolved in 100 ml of diethyl ether and a 3 M solution of methyl magnesium iodide in diethyl ether was added dropwise at 10° C. until the reaction had gone to completion. For work-up, the mixture was poured into ice-water and extracted with ethyl acetate, the combined organic phases were dried and concentrated and the residue was recrystallized from ethyl acetate. This gave 0.9 g (31%) of the title compound. m.p.: 124–127° C.

EXAMPLE 46

1-Benzyl-3-(5-methoxycarbonyl-2-furyl)-5-methylpyrazole and isomer 46a) Methyl 5-(1,3-dioxobutyl)furan-2-carboxylate: Over a period of 90 min, 130 g (0.5 mol) of tin(IV) chloride were added dropwise to a mixture of 31.5 g (0.25 mol) of methyl furan-2-carboxylate and 102 g (1 mol) of acetic anhydride which had been cooled to 0° C. After 16 h of stirring at RT, the mixture was cooled to 0° C., 20 ml of 30% strength hydrochloric acid were added dropwise and the mixture was subsequently stirred at RT for 3 h. The resulting mixture was poured into 200 ml of water and extracted repeatedly with ethyl acetate. The combined organic extracts were washed with water, dried and concentrated. The residue was chromatographed over silica gel using dichloromethane. The main fraction was recrystallized from isopropanol. This gave 19 g (36%) of the title compound. m.p.: 111–112° C. 46b) 1-Benzyl-3-(5-methoxycarbonyl-2-furyl)-5-methylpyrazole and isomer: 8 g (38.1 mmol) of methyl 5-(1,3-dioxobutyl)furan-2-carboxylate, 5.1 g (41.9 mmol) of benzylhydrazine and 1 ml of acetic acid in 150 ml of ethanol were heated under reflux for 2 h. For work-up, the mixture was concentrated, the residue was taken up in methylene chloride and the solution was washed with 2N aqueous sodium hydroxide solution, dried with sodium sulfate and concentrated. The oil that remained crystallized overnight and was recrystallized from a little isopropanol. This gave 7.95 g (70%) of 1-benzyl-3-(5-methoxycarbonyl-2-furyl)-5-methylpyrazole as a mixture with the isomeric 1-benzyl-5-(5-methoxycarbonyl-2-furyl)-3-methylpyrazole. m.p.: 65–66° C.

EXAMPLE 47

1-Benzyl-3-(2-furyl)-5-trifluoromethylpyrazole: 10 g (48.5 mmol) of 4,4,4-trifluoro-1-(2-furyl)-1,3-butadione, 7.5 g (53.4 mmol) of benzylhydrazine and 0.5 ml of acetic acid in 75 ml of ethanol were heated under reflux for 2 h. The mixture was concentrated, the residue was dissolved in dichloromethane, the solution was extracted alkaline and the organic phase was subsequently dried and concentrated. The residue was purified over silica gel using n-hexane/ethyl acetate (5:1). This gave 9.0 g (64%) of 1-benzyl-5-(2-furyl)-3-trifluoromethylpyrazole, in addition to 4.0 g of uncyclized hydrazone. This hydrazone was dissolved in 200 ml of methanol and heated under reflux with 1 ml of conc. sulfuric acid for 2 h. The mixture was subsequently concentrated, admixed with water and extracted with dichloromethane, and the organic phase was dried and concentrated once more. This gave 3.1 g (22%) of 1-benzyl-3-(2-furyl)-5-trifluoromethylpyrazole.

$^1$H-NMR (D$_6$-DMSO): δ=5.51 (s, 2H, CH$_2$), 6.60 (dd, 1H, H-4'), 6.92 (d, 1H, H-3'), 7.10-7.43 (m, 6H, phenyl-H, H-4), 7.75 (d, 1H, H-5')

EXAMPLE 48

1-Benzyl-3-(5-formyl-2-furyl)-5-trifluoromethylpyrazole: 10 ml of dry DMF were initially charged at 10° C., 1.9 g (12.4 mmol) of phosphorus oxychloride were added dropwise and the mixture was stirred for 30 min. A solution of 3 g (10.3 mmol) of 1-benzyl-3-(2-furyl)-5-trifluoromethylpyrazole in 10 ml of DMF was added dropwise, and the mixture was stirred at RT overnight. The mixture was poured into ice-water and adjusted to pH 9 using potassium carbonate solution. The precipitated product was filtered off with suction and dried in a vacuum drying cabinet at 50° C. This gave 3.3 g (100%) of the title compound. m.p.: 76.5–77.5° C.

EXAMPLE 49

1-Benzyl-3-(5-hydroxymethyl-2-furyl)-5-trifluoromethylpyrazole: 3 g (9.36 mmol) of 1-benzyl-3-(5-formyl-2-furyl)-5-trifluoromethylpyrazole were dissolved in 80 ml of methanol, 0.35 g (9.36 mmol) of sodium borohydride were added in portions and the mixture was stirred at RT for 1 h. The mixture was subsequently concentrated, the residue was admixed with water and methylene chloride, the methylene chloride phase was separated off, dried and concentrated and the residue was chromatographed over silica gel using dichloromethane. This gave 1.6 g (53%) of the title compound.

$^1$H-NMR (D$_6$-DMSO): δ=4.43 (d, 2H, CH$_2$O), 5.30 (t, 1H, OH), 5.52 (s, 2H, CH$_2$-phenyl), 6.41 (d, 1H, H-4'), 6.83 (d, 1H, H-3'), 7.13–7.21 (m, 2H, phenyl-H), 7.25 (s, 1H, H-4), 7.30-7.43 (m, 3H, phenyl-H)

EXAMPLE 50

3-(5–Carboxy-2-furyl)-1-(4-trifluoromethylpyrimidin-2-yl)indazole hydrochloride: 1.3 g (5.7 mmol) of 3-(5-carboxy-2-furyl)indazole together with 1.3 g (11.4 mmol) of potassium tert-butoxide were dissolved in 5 ml of dry DMF and admixed with 2-chloro-4-trifluoromethylpyrimidine dissolved in 5 ml of DMF. The mixture was stirred at 60° C. the hydrochloride was precipitated from the aqueous phase by addition of 1N hydrochloric acid. This gave 420 mg (25%) of the title compound. m.p.: 258–261° C.

Pharmacological Investigations

1. Activation of the soluble guanylate cyclase

The activation of the sGC, which catalyzes the conversion of GTP into cyclic guanosine monophosphate cGMP and pyrophosphate, by the compounds according to the invention was quantified with the aid of an enzyme immunoassay "EIA" from Amersham. For this purpose the substances to be tested were initially incubated with sGC in microtiter plates, and the amount of the cGMP formed was then determined.

The sGC which was employed had been isolated from bovine lung (see *Methods in Enzymology*, Volume 195, p. 377). The test solutions (100 μl per well) contained 50 mM triethanolamine "TEA" buffer (pH 7.5), 3 mM MgCl$_2$, 3 mM reduced glutathione "GSH," 0.1 mM GTP, 1 mM 3-isobutyl-1-methylxanthine "IBMX," suitably diluted enzyme solution and the substance to be tested or, in the control experiments, the solvent. The substances to be tested were dissolved in dimethyl sulfoxide "DMSO" and the solution was diluted with DMSO/water, so that the final concentration of the substance to be tested in the test solution was 50 μM. The DMSO concentration in the test solution was 5% (v/v). The reaction was initiated by addition of the sGC. The reaction mixture was incubated at 37° C. for 15 to 20 minutes and then stopped by ice-cooling and addition of the stop reagent (50 mM EDTA, pH 8.0). An aliquot of 50 μl was taken and used for determining the cGMP content using the acetylation protocol of the Amersham cGMP-EIA kit. The absorption of the samples was measured at 450 nm (reference wavelength 620 nm) in a microtiter plate reader. The cGMP concentration was determined using a standard curve which was obtained under the same test conditions. The activation of sGC by a test substance is reported as the n-fold stimulation of the basal enzyme activity which was found in the control experiments (using solvent instead of test substance). This is calculated using the formula:

$$\text{n-fold stimulation} = [\text{cGMP}]_{\text{test substance}} / [\text{cGMP}]_{\text{control}}.$$

The following values were determined:

| Compound | Concentration | n-fold stimulation |
| --- | --- | --- |
| Example 6 | 10 μM | 3.3-fold |
| Example 7 | 100 μM | 5.5-fold |
| Example 21 | 100 μM | 3-fold |
| Example 25 | 10 μM | 2.8-fold |
| Example 40 | 100 μM | 2.4-fold |
| Example 44 | 100 μM | 3.2-fold |

2. Relaxation of rat aorta

For this test, normotensive male Wistar-Kyoto rats were sacrificed by a blow to the neck. The abdominal cavity and the thorax were opened by a medium sternotomy. The descending aorta was subsequently removed, freed of connective tissue and divided into 8 rings of a length of approximately 4 mm. The tip of a pair of tweezers was introduced into the lumen of 4 of the 8 rings. The endothelium was removed by carefully rolling the rings over the tip of the pair of tweezers. All 8 aorta rings (4 with endothelium and 4 without endothelium) were subsequently suspended in an organ bath (Schuler-Organbad; Hugo Sachs Elektronik) at a constant temperature of 37° C. for the isometric determination of the contractile tone. For 30 minutes, the rings were calibrated at a resting tension of 1 g in carbonated (95% $O_2$; 5% $CO_2$) Krebs-Henseleit solution (composition: $Na^+$ 144.0 mM; $K^+$ 5.9 mM; $Cl^-$ 126.9 mM; $Ca^{2+}$ 1.6 mM; $Mg^{2+}$ 1.2 mM; $H_2PO_4^-$ 1.2 mM; $SO_4^{2-}$ 1.2 mM; $HCO_3^-$ 25.0 mM; D-glucose 11.1 mM) of pH 7.4. Additionally, 1 μmol/l of indomethacin were added to the Krebs-Henseleit solution to inhibit prostaglandin biosynthesis. The rings were subsequently precontracted by addition of phenylephrine (concentration in the solution: 1 μM) and the endothelium-dependent relaxation or the functional loss of the endothelium was tested by addition of acetylcholine (concentration in the solution: 1 μM). After a 30-minute washing period, the rings were then again precontracted by addition of phenylephrine (1 μM), and the relaxing action of the test substances of the formula I was determined by administration of cumulative doses of the latter. The data were evaluated by standard methods. Reported is the concentration $IC_{50}$ by which contraction is inhibited by 50% (50% relaxation).

The following values were determined:

| Compound | | $IC_{50}$ |
| --- | --- | --- |
| Example 40 | Ring with endothelium | 2.4 μM |
| Example 40 | Ring without endothelium | 0.2 μM |

The above embodiments and description are included to illustrate the invention, and are not intended to express or imply any limits upon the scope of the invention, nor of its equivalents.

We claim:
1. A compound of the formula I:

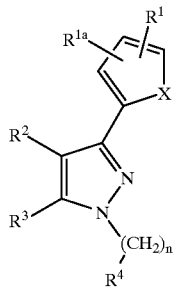

(I)

in which

X is O;

$R^1$ is $OR^6$, $NR^7R^8$, CO—$OR^9$, CO—$R^{10}$, CO—$NR^{11}R^{12}$, —$OR^{11}$, $S(O)_m$—$R^{13}$, $S(O)_2$—$NR^{14}R^{15}$, CN, $C_3$–$C_{10}$)-alkyl, $(C_6$–$C_{14})$-aryl, $(C_6$–$C_{14})$-aryl-$(C_1$–$C_4)$-alkyl, $(C_3$–$C_7)$-cycloalkyl, $(C_3$–$C_7)$-cycloalkyl-$(C_1$–$C_4)$-alkyl, Het, or Het-$(C_1$–$C_4)$-alkyl, wherein alkyl is substituted by one or more substituents selected from the group consisting of halogen, $OR^6$, $NR^7R^8$, CO—$OR^9$, CO—$R^{10}$, CO—$NR^{11}R^{12}$, CO—$NR^{12}$—$OR^{11}$, $S(O)_m$—$R^{13}$$S(O)_2$—$NR^{14}R^{15}$, $NO_2$, CN, and $CF_3$, and wherein aryl, arylalkyl, cycloalkyl, cycloalkylalkyl, Het, and Het-alkyl are unsubstituted or substituted by one or more substituents $R^5$, and wherein $R^9$ present in the group $COOR^9$ is $(C_1$–$C_{10})$-alkyl, $(C_8$–$C_{14})$-aryl, $(C_6$–$C_{14})$-aryl-$(C_1$–$C_4)$-alkyl, $(C_3$–$C_7)$-cycloalkyl, $(C_3$–$C_7)$-cycloalkyl-$(C_1$–$C_4)$-alkyl, Het or Het-$(C_1$–$C_4)$-alkyl, wherein alkyl is substituted by one or more identical or different substituents selected from the group consisting of halogen, $OR^{18}$, $NR^{19}R^{20}$, CO—$OR^{21}$, CO—$R^{22}$, CO—$NR^{23}R^{24}$, CO—$NR^{24}$—$OR^{23}$, $S(O)_m$—$R^{25}$, $S(O)_2$—$NR^{26}R^{27}$, $NO_2$, CN, and $CF_3$, and wherein aryl, arylalkyl, cycloalkyl, cycloalkylalkyl, Het and Het-alkyl are unsubstituted or are substituted by one or more identical or different substituents selected from the group consisting of halogen, $(C_1$–$C_5)$-alkyl, $OR^{18}$, $NR^{19}R^{20}$, CO—$OR^{21}$, CO—$R^{22}$, CO—$NR^{23}R^{24}$, CO—$NR^{24}$—$OR^{23}$, $S(O)_m$—$R^{25}$, $S(O)_2$—$NR^{26}R^{27}$, $NO_2$, CN, and $CF_3$;

$R^{1a}$ is hydrogen $OR^6$, $NR^7R^8$, CO—$OR^9$, CO—$R^{10}$, CO—$NR^{11}R^{12}$, CO—$NR^{12}$—$OR^{11}$, $S(O)_m$—$R^{13}$, $S(O)_2$—$NR^{14}R^{15}$, CN, $(C_1$–$C_{10})$-alkyl, $(C_8$–$C_{14})$-aryl, $(C_6$–$C_{14})$-aryl-$(C_1$–$C_4)$-alkyl, $(C_3$–$C_7)$-cycloalkyl, $(C_3$–$C_7)$-cycloalkyl-$(C_1$–$C_4)$-alkyl, Het, or Het-$(C_1$–$C_4)$-alkyl, wherein alkyl, aryl, arylalkyl, cycloalkyl, cycloalkylalkyl, Het, and Het-alkyl are unsubstituted or substituted by one or more substituents $R^5$;

$R^2$ and $R^3$ together with the carbon atoms which carry them form a 5- to 7-membered carbocyclic ring which is saturated or comprises one or more double bonds, and which is unsubstituted or substituted by one or more substituents $R^5$;

$R^4$ is hydrogen, $(C_1$–$C_{10})$-alkyl, $(C_6$–$C_{14})$-aryl, $(C_6$–$C_{14})$-aryl-$(C_1$–$C_4)$-alkyl, $(C_3$–$C_7)$-cycloalkyl, $(C_3$–$C_7)$-cycloalkyl-$(C_1$–$C_4)$alkyl, Het, or Het-$(C_1$–$C_4)$-alkyl, wherein alkyl, aryl, arylalkyl, cycloalkyl, cycloalkylalkyl, Het, and Het-alkyl are unsubstituted or substituted by one or more substituents $R^5$, and where n is O, $R^4$ is not hydrogen;

n is 0, 1 or 2;

Het is a 5- to 7-membered, saturated, or unsaturated heterocycle;

$R^5$ is halogen, $(C_1$–$C_5)$-alkyl, $OR^6$, $NR^7R^8$, CO—$OR^9$, CO—$R^{10}$, CO—$NR^{11}R^{12}$, CO—$NR^{12}$—$OR^{11}$, $S(O)_m R^{13}$, $S(O)_2$—$NR^{14}R^{15}$, $NO_2$, CN, or $CF_3$, wherein radicals $R^5$ that occur more than once are identical or different;

$R^6$, $R^7$, $R^8$, $R^{11}$, and $R^{14}$ are identical or different, and are hydrogen, $(C_1$–$C_{10})$-alkyl, $(C_6$–$C_{14})$-aryl, $(C_6$–$C_{14})$-aryl-$(C_1$–$C_4)$-alkyl, $(C_3$–$C_7)$-cycloalkyl, $(C_3$–$C_7)$-cycloalkyl-$(C_1$–$C_4)$-alkyl, Het, Het-$(C_1$–$C_4)$-alkyl, CO—$R^{16}$, or $S(O)_2$—$R^{17}$, wherein alkyl, aryl, arylalkyl, cycloalkyl, cycloalkylalkyl, Het, and Het-alkyf representing $R^6$, $R^7$, $R^8$, $R^{11}$, and $R^{14}$ are in each case unsubstituted or substituted by one or more identical or different substituents selected from the group consisting of halogen, $(C_1$–$C_5)$-alkyl, $OR^{28}$, $NR^{19}R^{20}$, CO—$OR^{21}$, CO—$R^{22}$, CO—$NR^{23}R^{24}$, CO—$NR^{24}$—$OR^{23}$, $S(O)_m$–$R^{25}$, $S(O)_2$—$NR^{26}R^{27}$, $NO_2$, CN, and $CF_3$, and wherein radicals $R^6$, $R^7$, $R^8$, $R^{11}$, and $R^{14}$ that occur more than once are identical or different;

$R^9$, other than $R^9$ present in the group $COOR^9$ representing $R^1$, $R^{10}$, $R^{12}$, $R^{13}$ and $R^{15}$ are identical or different, and are hydrogen, $(C_1$–$C_{10})$-alkyl, $(C_6$–$C_{14})$-aryl, $(C_8$–$C_{14})$-aryl-$(C_1$–$C_4)$-alkyl, $(C_3$–$C_7)$-cycloalkyl, $(C_3$–$C_7)$-cycloalkyl-$(C_1$–$C_4)$-alkyl, Het, or Het-$(C_1$–$C_4)$-alkyl, wherein alkyl, aryl, arylalkyl, cycloalkyl, cycloalkylalkyl, Het, and Het-alkyl representing $R^9$, $R^{10}$, $R^{12}$, $R^{13}$, and $R^{15}$ are in each case unsubstituted or substituted by one or more identical or different substituents selected from the group consisting of halogen, $(C_1-C_5)$-alkyl, $OR^{18}$, $NR^{19}R^{20}$, $CO-OR^{21}$, $CO-R^{22}$, $CO-NR^{23}R^{24}$, $CO-NR^{24}-OR^{23}$, $S(O)_m-R^{25}$, $S(O)_2-NR^{26}R^{27}$, $NO_2$, CN, and $CF_3$, and wherein radicals $R^9$, $R^{10}$, $R^{12}$, $R^{13}$, and $R^{15}$ that occur more than once are identical or different;

or two radicals $R^7$ with $R^8$, two radicals $R^{11}$ with $R^{12}$, or two radicals $R^{14}$ with $R^{15}$, in each case together with the nitrogen atom which carries the two radicals, form a 5- to 7-membered, saturated or unsaturated heterocyclic ring which further comprises zero or one additional ring heteroatom selected from the group consisting of nitrogen, oxygen and sulfur, and the heterocyclic ring is unsubstituted or substituted by one or more identical or different substituents selected from the group consisting of $(C_1-C_4)$-alkyl and halogen;

$R^{16}$ is hydrogen, $(C_1-C_6)$-alkyl, $(C_3-C_7)$-cycloalkyl, $(C_3-C_7)$-cycloalkyl-$(C_1-C_5)$-alkyl, $(C_6-C_{14})$-aryl, $(C_1-C_4)$-aryl-$(C_1-C_4)$-alkyl, Het, or Het-$(C_1-)$-alkyl;

$R^{17}$ is $(C_1-C_6)$-alkyl, $(C_3-C_7)$-cycloalkyl, $(C_3-C_7)$-Cycloalkyl-$(C_1-C_4)$-alkyl, $(C_1-C_{14},)$-aryl, $(C_6-C_{14})$-aryl-$(C_1-C_4)$-alkyl, Het, or Het-$(C_1-C_4)$-alkyl;

$R^{18}$, $R^{19}$, $R^{20}$, $R^{23}$ and $R^{26}$ are identical or different, and are hydrogen, $(C_1-C_{10})$-alkyl, $(C_3-C_7)$-cycloalkyl, $(C_3-C_7)$-cycloalkyl-$(C_1-C_4)$-alkyl, $(C_6-C_{14})$-aryl, $(C_6-C_{14})$-aryl-$(C_1-C_4)$-alkyl, the radical Het, the radical Het-$(C_1-C_4)$-alkyl, $CO-R^{16}$ or $S(O)_2-R^{17}$, wherein radicals $R^{18}$, $R^{19}$, $R^{20}$, $R^{23}$, and $R^{26}$ that occur more than once are identical or different;

$R^{21}$, $R^{22}$, $R^{24}$, $R^{25}$ and $R^{27}$ are identical or different, and are hydrogen, $(C_1-C_{10})$-alkyl, $(C_3-C_7)$-cycloalkyl, $(C_3-C_7)$-cycloalkyl-$(C_1-C_4)$-alkyl, $(C_6-C_{14})$-aryl, $(C_6-C_{14})$-aryl-$(C_1-C_4)$-alkyl, Het, or Het-$(C_1-C_4)$-alkyl, wherein radicals $R^{21}$, $R^{22}$, $R^{24}$, $R^{25}$ and $R^{27}$ that occur more than once are identical or different;

or two radicals $R^{19}$ with $R^{20}$, two radicals $R^{23}$ with $R^{24}$, or two radicals $R^{26}$ with $R^{27}$, in each case together with the nitrogen atom which carries the two radicals, form a 5- to 7-membered, saturated or unsaturated heterncyclic ring which further comprises zero or one additional ring heteroatom selected from the group consisting of nitrogen, oxygen and sulfur, and the heterocyclic ring is unsubstituted or substituted by one or more identical or different substituents selected from the group consisting of $(C_1-C_4)$-alkyl and halogen;

m is 0, 1 or 2;

a stereoisomer of the compound of formula I, or a physiologically acceptable salt of any of the forgoing.

2. The compound of the formula I as claimed in claim 1, in which $R^2$ and $R^3$ together with the carbon atoms which carry them form a benzene ring which is unsubstituted or substituted by one or more identical or different slibstituents $R^5$, a stereoisomer thereof, or a physiologically acceptable salt of any of the foregoing.

3. The compound of the formula I as claimed in claim 1, in which $R^{1a}$ is hydrogen, a stereoisomer thereof, or a physiologically acceptable salt of any of the foregoing.

4. The compound of the formula I as claimed in claim 1, in which $R^1$ is $(C_3-C_{10})$-alkyl which is substituted by hydroxyl, or is $CO-OR^9$ or is $CO-NR^{11}R^{12}$, a stereoisomer thereof, or a physiologically acceptable salt of any of the foregoing.

5. The compound of the formula I as claimed in claim 1, in which $R^{11}$ is hydrogen and $R^{12}$ is unsubstituted $(C_1-C_4)$-alkyl, $(C_1-C_4)$-alkyl which is substituted by a radical selected from the group consisting of $OR_{18}$, $NR^{19}R^{20}$ and $CO-NR^{23}R^{24}$, 5- or 6-membered heteroaryl, unsubstituted phenyl or phenyl which is substituted by one, two or three identical or different radicals selected from the group consisting of halogen, $(C_1-C_5)$-alkyl, $OR^{18}$, $NR^{19}R^{20}$, $CO-OR^{21}$, $CO-R^{22}$, $CO-NR^{23}R^{24}$, $S(O)_m-R^{25}$, $S(O)_2-NR^{26}R^{27}$, $NO_2$, CN and $CF_3$, a stereoisomer thereof, or a physiologically acceptable salt of any of the foregoing.

6. The compound as claimed in claim 1, wherein at least one of $R^1$ and $R^{1a}$ is $COOR^9$, $CONR^{11}R^{12}$, $(C_3-C_{10})$-alkyl, or $(C_6-C_{14})$-aryl-$(C_1-C_4)$-alkyl, or $R^{1a}$ is $(C_1-C_2)$-alkyl.

7. A pharmaceutical composition, comprising an efficacious amount of one or more compounds of formula I as claimed in claim 1, a mixture of two or more stereoisomers of the compound of formula I, or a physiologically acceptable salt thereof, together with at least one pharmaceutically acceptable carrier.

8. A method of activating soluble guanylate cyclase in a human or animal patient in need of such activation, comprising administering to the patient an efficacious amount of a compound of formula I

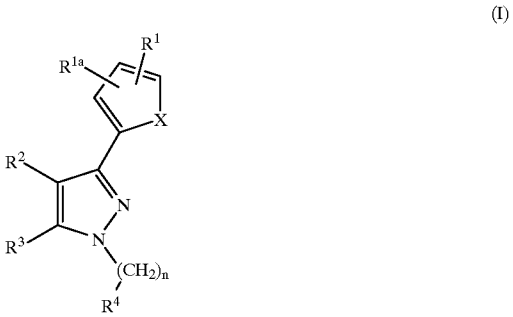

(I)

in which

X is O;

$R^1$ and $R^8$ are identical or different, and are hydrogen, halogen, $OR^6$, $NR^7R^8$, $CO-OR^9$, $CO-R^{10}$, $CO-NR^{11}R^{12}$, $C)-NR^{12}-OR^{11}$, $S(O)_m-R^{13}$, $S(O)_2-NR^{14}R_{15}$, CN, $(C_3-C_{10})$-alkyl, $(C_6-C_{14})$-aryl, $(C_6-C_{14})$-aryl-$(C_1-C_4)$-alkyl, $(C_3-C_7)$-cycloalkyl, $(C_3-C_7)$-cycloalkyl-$(C_1-C_4)$-alkyl, Het, or Het-$(C_1-C_4)$-alkyl, wherein alkyl, aryl, arylalkyl, cycloalkyl, cycloalkylalkyl, Het, and Het-alkyl are in each case unsubstituted or substituted by one or more substituents $R^5$; or $R^1$ is $NO_2$ in the case when simultaneously $R^{1a}$ is hydrogen, $R^2$ and $R^3$ together with the carbon atoms which carry them form an unsubstituted benzene ring or a benzene ring which is substituted by one or more substituents $R^5$, and $-(CH_2)_n-R^4$ is different from unsubstituted phenyl;

$R^2$ and $R^3$ are identical or different, and are hydrogen, $(C_1-C_{10})$-alkyl, $(C_6-C_{14})$-aryl, $(C_6-C_{14})$-aryl-$(C_1-C_4)$-alkyl, $(C_3-C_7)$-cycloalkyl, $(C_3-C_7)$-cycloalkyl-$(C_1-C_4)$-alkyl, Het, or Het-$(C_1-C_4)$-alkyl, wherein alkyl, aryl, arylalkyl, cycloalkyl, cycloalkylalkyl, Het, and Het-alkyl representing $R^2$ or $R^3$ are unsubstituted or substituted by one or more substituents $R^5$;

or $R^2$ and $R^3$ together with the carbon atoms which carry them form a 5- to 7-membered carbocyclic ring which is saturated or comprises one or more double bonds, and which is unsubstituted or substituted by one or more substituents $R^5$;

$R^4$ is hydrogen, $(C_1-C_{10})$-alkyl, $(C_6-C_{14})$-aryl, $(C_6-C_{14})$-aryl-$(C_1-C_4)$-alkyl, $(C_3-C_7)$-cycloalkyl, $(C_3-C_7)$- cycloalkyl-($C_1$–$C_4$)-alkyl, Het, or Het-($C_1$–$C_4$)-alkyl, wherein alkyl, aryl, arylalkyl, cycloalkyl, cycloalkylalkyl, Het, and Het-alkyl are unsubstituted or substituted by one or more substituents $R^5$, and where n is 0, $R^4$ is not hydrogen;

n is 0, 1 or 2;

Het is a 5- to 7-membered, saturated, or unsaturated heterocycle;

$R^5$ is halogen, ($C_1$–$C_5$)-alkyl, $OR^6$, $NR^7R^8$, CO—$OR^9$, CO—$R^{10}$, CO—$NR^{11}R^{12}$, CO—$NR^{12}$—$OR^{11}$, $S(O)_m$—$R^{13}$, $S(O)_2$—$R^{14}R^{15}$, $NO_2$, CN, or $CF_3$, wherein radicals $R^5$ that occur more than once are identical or different;

$R^6$, $R^7$, $R^8$, $R^{11}$, and $R^{14}$ are identical or different, and are hydrogen, ($C_1$–$C_{10}$)-alkyl, ($C_6$–$C_{14}$)-aryl, ($C_6$–$C_{14}$)-aryl-($C_1$–$C_4$)-alkyl, ($C_3$–$C_7$)cycloalkyl, ($C_3$–$C_7$)-cycloalkyl-($C_1$–$C_4$)-alkyl, Het, Het-($C_1$–$C_4$)-alkyl, CO—$R^{16}$, or $S(O)_2$—$R^{17}$, wherein alkyl, aryl, arylalkyl, cycloalkyl, cycloalkylalkyl, Het, and Het-alkyl are in each case unsubstituted or substituted by one or more identical or different substituents selected from the group consisting of halogen, ($C_1$–$C_5$)-alkyl, $OR^{18}$, $NR^{19}R^{20}$, CO—$OR^{21}$, CO—$R^{22}$, CO—$NR^{23}R^{24}$, CO—$NR^{24}$—$OR^{23}$, $S(O)_m$—$R^{25}$, $S(O)_2$—$NR^{26}R^{27}$, $NO_2$, CN, and $CF_3$, and wherein radicals $R^6$, $R^7$, $R^8$, $R^{11}$, and $R^{14}$ that occur more than once are identical or diferent;

$R^9$, $R^{10}$, $R^{12}$, $R^{13}$ and $R^{15}$ are identical or different, and are hydrogen, ($C_1$–$C_{10}$)-alkyl, ($C_6$–$C_{14}$)-aryl, ($C_1$–$C_{14}$)-aryl-($C_1$–$C_4$)-alkyl, ($C_3$–$C_7$)-cycloalkyl, ($C_3$–$C_7$)-cycloalkyl-($C_1$–$C_4$)-alkyl, Het, or Het-($C_1$–$C_4$)-alkyl, wherein alkyl, aryl, arylalkyl, cycloalkyl, cycloalkylalkyl, Het, and Het-alkyl are in each case unsubstituted or substituted by one or more identical or different substituents selected from the group consisting of halogen, ($C_1$–$C_5$)-alkyl, $OR^{18}$, $NR^{19}R^{20}$, CO—$OR^{21}$, CO—$R^{22}$, CO—$NR^{23}R^{24}$, CO—$NR^{24}$—$OR^{23}$, $S(O)_m$—$R^{25}$, $S(O)_2$—$NR^{26}BR^{27}$, $NO_2$, CN, and $CF_3$, and wherein radicals $R^9$, $R^{10}$, $R^{12}$, $R^{13}$, and $R^{15}$ that occur more than once are identical or different;

or two radicals $R^7$ with $R^8$, two radicals $R^{11}$ with $R^{12}$, or two radicals $R^{14}$ with $R^{15}$, in each case together with the nitrogen atom which carries the two radicals, form a 5- to 7-membered, saturated or unsaturated heterocyclic ring which further comprises zero or one additional ring heteroatom selected from the group consisting of nitrogen, oxygen and sulfur, and the heterocyclic ring is unsubstituted or substituted by one or more identical or different substituents selected from the group consisting of ($C_1$–$C_4$)-alkyl and halogen;

$R^{16}$ is hydrogen, ($C_1$–$C_6$)-alkyl, ($C_3$–$C_7$)-cycloalkyl, ($C_3$–$C_7$)-cycloalkyl-($C_1$–$C_4$)-alkyl, ($C_6$–$C_{14}$)-aryl, ($C_6$–$C_{14}$)-aryl-($C_1$–$C_4$)-alkyl, Het, or Het-($C_1$–$C_4$)-alkyl;

$R^{17}$ is ($C_1$–$C_6$)-alkyl, ($C_3$–$C_7$)-cycloalkyl, ($C_3$–$C_7$)-cycloalkyl-($C_1$–$C_4$)-alkyl, ($C_6$–$C_{14}$)-aryl, ($C_6$–$C_{14}$)-aryl-($C_1C_4$)-alkyl, Het, or Het-($C_1$–$C_4$)-alkyl;

$R^{18}$, $R^{19}$, $R^{20}$, $R^{23}$ and $R^{25}$ are identical or different, and are hydrogen, ($C_1$–$C_{10}$)-alkyl, ($C_3$–$C_7$)-cycloalkyl ($C_3$–$C_7$)-cycloalkyl-($C_1$–$C_4$)-alkyl, ($C_6$–$C_{14}$)-aryl, ($C_6$–$C_{14}$)-aryl-($C_1$–$C_4$)-alkyl, the radical Het, the radical Het- ($C_1$–$C_4$)-alkyl, CO—$R^{16}$ or $S(O)_2$—$R^{17}$, wherein radicals $R^{18}$, $R^{19}$, $R^{20}$, $R^{23}$, and $R^{26}$ that occur more than once are identical or different;

$R^{21}$, $R^{22}$, $R^{24}$, $R^{25}$ and $R^{27}$ are identical or different, and are hydrogen, ($C_1$–$C_{10}$)-alkyl, ($C_3$–$C_7$)-cycloalkyl, ($C_3$–$C_7$)-cycloalkyl-($C_1$–$C_4$)-alkyl, ($C_6$–$C_{14}$)aryl, ($C_6$–$C_{14}$)-aryl-($C_1$–$C_4$)-alkyl, Het, or Het-($C_1$–$C_4$)-alkyl, wherein radicals $R^{21}$, $R^{22}$, $R^{24}$, $R^{25}$, and $R^{27}$ that occur more than once are identical or different;

or two radicals $R^{19}$ with $R^{20}$, two radicals $R^{23}$ with $R^{24}$, or two radicals $R^{26}$ with $R^{27}$ in each case together with the nitrogen atom which carries the two radicals, form a 5- to 7-membered, saturated or unsaturated heterocyclic ring which further comprises zero or one additional ring heteroatom selected from the group consisting of nitrogen, oxygen and sulfur, and the heterocyclic ring is unsubstituted or substituted by one or more identical or different substituents selected from the group consisting of ($C_1$–$C_4$)-alkyl and halogen;

m is 0, 1 or 2;

a stereoisomer of the compound of formula I, a mixture of two or more stereolsomers of the compound of formula I, or a physiologically acceptable salt of any of the forgoing;

except for compounds of the formula I where the following radicals simultaneously have the following meanings: $R^1$ is a radical in the 5-position of the ring comprising X, and is selected from the group consisting of hydrogen, ($C_1$–$C_3$)-alkyl, COOH, CO—O—($C_1$–$C_3$)-alkyl, $CH_2$—OH, $CH_2$—O—($C_1$–$C_3$)-alkyl and halogen; $R^{1a}$ is hydrogen; $R^2$ and $R^3$ together with the carbon atoms which carry them are a benzene ring which is unsubstituted or monosubstituted by a radical selected from the group consisting of ($C_1$–$C_3$)-alkyl, halogen, hydroxyl and ($C_1$–$C_3$)-alkoxy; n is the number 1; $R^4$ is unsubstituted phenyl or phenyl which is monosubstituted by a radical selected from the group consisting of ($C_1$–$C_3$)-alkyl, halogen, hydroxyl and ($C_1$–$C_3$)-alkoxy; and except for the compound of the formula I wherein the radicals simultaneously have the following meanings: X is S; $R^1$ is a chlorine atom which is attached to the 5-position of the ring comprising X; $R^{1a}$ is hydrogen; $R^2$ is methyl; $R^3$ is hydrogen; n is 0; $R^4$ is the radical $(CH_3)_2$N—CO—CH($CH_3$)—.

9. The method of claim 8, in which the patient is administered an efficacious amount of a compound of formula I, a mixture of two or more stereoisomers of the compound of formula I or a physiologically acceptable salt thereof, to prevent cardiovascular disease, endothelia dysfunction, diastolic dysfunction, atherosclerosis, hypertension, angina pectoris, thromboses, restenoses, myocardial infarction, stroke, cardiac insufficiency, pulmonary hypertonia, erectile dysfunction, asthma bronchiale, chronic kidney insufficiency, diabetes, cirrhosis of the liver, restricted memory performance, or leaming disability.

10. The method of claim 8, in which the patient is administered an efficacious amount of a compound of formula I, a mixture of two or more stereoisomers of the compound of formula I, or a physiologically acceptable salt thereof, to treat cardiovascular disease, endothelial dysfunction, diastolic dysfunction, atherosclerosis, hypertension, angina pectoris, thromboses, restenoses, myocardial infarction, stroke, cardiac insufficiency, pulmonary hypertonia, erectile dysfunction, asthma bronchiale, chronic kidney insufficiency, diabetes, cirrhosis of the liver, restricted memory performance, or learning disability.

11. A method of activating soluble guanylate cyclase in a human or animal patient in need of such activation, comprising administering to the patient an efficacious amount of a compound of formula I as claimed in claim 1, a mixture of two or more stereoisomers of the compound of formula I, or a physiologically acceptable salt of any of the foregoing.

12. A method of preventing cardiovascular disease, endothelial dysfunction, diastolic dysfunction, atherosclerosis, hypertension, angina pectoris, thromboses, restenoses, myocardial infarction, stroke, cardiac insufficiency, pulmonary hypertonia, erectile dysfunction, asthma bronchiale, chronic kidney insufficiency, diabetes, cirrhosis of the liver, restricted memory performance, or learning disability, in which the patient is administered an efficacious amount of a compound of formula I as claimed in claim 1, a mixture of two or more stereoisomers of the compound of formula I, or a physiologically acceptable salt of any of the foregoing.

13. A method of treating cardiovascular disease, endothelial dysfunction, diastolic dysfunction. atherosclerosis, hypertension, angina pectoris, thromboses, restenoses, myocardial infarction, stroke, cardiac insufficiency, pulmonary hypertonia, erectile dysfunction, asthma bronchiale, chronic kidney insufficiency, diabetes, cirrhosis of the liver, restricted memory performance, or learning disability, in which the patient is administered an efficacious amount of a compound of formula I as claimed in claim 1, a mixture of two or more stereoisomers of the compound of formula I, or a physiologically acceptable salt of any of the foregoing.

* * * * *

UNITED STATES PATENT AND TRADEMARK OFFICE
CERTIFICATE OF CORRECTION

PATENT NO. : 6,162,819
DATED : December 19, 2000
INVENTOR(S) : Ursula Schindler et al.

It is certified that error appears in the above-identified patent and that said Letters Patent is hereby corrected as shown below:

Title page,
Item [57], ABSTRACT,
Lines 14-15, "formula 1" should read -- formula I --.

Column 33,
Line 57, "–$OR^{11}$" should read -- $CO-NR^{12}-OR^{11}$ --, and "$C_3-C_{10}$)-" should read -- ($C_3-C_{10}$)- --.
Line 64, "$S(O)_m-R^{13}S(O)_2-NR^{14}R^{15}$" should read -- $S(O)_m-R^{13}$, $S(O)_2-NR^{14}R^{15}$ --.

Column 34,
Line 2, "($C_8-C_{14}$)-aryl" should read -- ($C_6-C_{14}$)-aryl --.
Line 19, "($C_8-C_{14}$)-aryl" should read -- ($C_6-C_{14}$)-aryl --.
Line 37, "n is O" should read -- n is 0 --.
Line 53, "alkyf" should read -- alkyl --.
Line 56, "$OR^{28}$" should read -- $OR^{18}$ --.
Line 64, "($C_8-C_{14}$)-aryl-($C_1-C_4$)-alkyl" should read -- ($C_6-C_{14}$)-aryl-($C_1-C_4$)-alkyl --.

Column 35,
Line 20, "($C_3-C_7$)-cycloalkyl-($C_1-C_5$)-alkyl" should read -- ($C_3-C_7$)-cycloalkyl-($C_1-C_4$)-alkyl --.
Line 21, "($C_1-C_4$)-aryl-($C_1-C_4$)-alkyl" should read -- ($C_6-C_{14}$)-aryl-($C_1-C_4$)-alkyl --, and "Het-($C_1-$,)-alkyl" should read -- Het-($C_1-C_4$)-alkyl --.
Line 23, "Cycloalkyl-($C_1-C_4$)-alkyl" should read -- cycloalkyl-($C_1-C_4$)-alkyl, and "($C_1-C_{14}$)-aryl" should read -- ($C_6-C_{14}$)-aryl --.
Lines 41-42, "heterncyclic" should read -- heterocyclic --.
Line 51, "forgoing" should read -- foregoing --.
Line 55, "slibstituents" should read -- substituents --.

Column 36,
Line 1, "$OR_{18}$" should read -- $OR^{18}$ --.
Line 37, "$R^8$" should read -- $R^{1a}$ --.
Line 38, "$CO-OR^9$;" should read -- $CO-OR^9$, --.
Line 39, "C)–$NR^{12}-OR^{11}$" should read -- $CO-NR^{12}-OR^{11}$ --.
Line 40, "$S(O)_2-NR^{14}R_{15}$" should read -- $S(O)_2-NR^{14}R^{15}$ --.

UNITED STATES PATENT AND TRADEMARK OFFICE
CERTIFICATE OF CORRECTION

PATENT NO.    : 6,162,819
DATED         : December 19, 2000
INVENTOR(S)   : Ursula Schindler et al.

It is certified that error appears in the above-identified patent and that said Letters Patent is hereby corrected as shown below:

Column 37,
Line 11, "S(O)$_2$–R$^{14}$R$^{15}$" should read -- S(O)$_2$–NR$^{14}$R$^{15}$ --.
Line 16, "(C$_3$–C$_7$)cycloalkyl" should read -- (C$_3$–C$_7$)-cycloalkyl --.
Line 29, "(C$_1$–C$_{14}$)-aryl-(C$_1$–C$_4$)-alkyl" should read -- (C$_6$–C$_{14}$)-aryl-(C$_1$–C$_4$)-alkyl --.
Line 37, "S(O)$_2$–NR$^{26}$BR$^{27}$" should read -- S(O)$_2$–NR$^{26}$R$^{27}$ --.
Line 58, "aryl-(C$_1$C$_4$)-alkyl" should read -- aryl-(C$_1$–C$_4$)-alkyl --.
Line 59, "R$^{25}$" should read -- R$^{26}$ --.
Line 60, after "(C$_3$–C$_7$)-cycloalkyl", insert a comma.

Column 38,
Line 6, after "R$^{27}$", insert a comma.
Line 17, "stereolsomers" should read -- stereoisomers --.
Line 42, after "formula I", insert a comma.
Line 43, "endothelia" should read -- endothelial --.

Column 39,
Line 11, "diastolic dysfunction." should read -- diastolic dysfunction, --.

Signed and Sealed this

Twenty-eighth Day of January, 2003

JAMES E. ROGAN
*Director of the United States Patent and Trademark Office*